US008812104B2

(12) United States Patent
Mokelke et al.

(10) Patent No.: US 8,812,104 B2
(45) Date of Patent: Aug. 19, 2014

(54) METHOD AND APPARATUS FOR AUTOMATED CONTROL OF PACING POST-CONDITIONING

(75) Inventors: Eric A. Mokelke, White Bear Lake, MN (US); James A. Esler, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 997 days.

(21) Appl. No.: 12/877,622

(22) Filed: Sep. 8, 2010

(65) Prior Publication Data

US 2011/0071584 A1 Mar. 24, 2011

Related U.S. Application Data

(60) Provisional application No. 61/245,067, filed on Sep. 23, 2009.

(51) Int. Cl.
*A61N 1/00* (2006.01)
*A61N 1/36* (2006.01)

(52) U.S. Cl.
CPC .................................... *A61N 1/36* (2013.01)
USPC ............................................................ 607/9

(58) Field of Classification Search
CPC ...... A61N 1/36; A61N 1/362; A61N 1/36146; A61N 1/3615; A61N 1/36153; A61N 1/36157; A61N 1/36167; A61N 1/36171; A61N 1/36175
USPC .............................................. 607/2, 4, 9, 10
See application file for complete search history.

(56) References Cited

U.S. PATENT DOCUMENTS

| | | | |
|---|---|---|---|
| 3,650,277 | A | 3/1972 | Sjostrand et al. |
| 4,587,975 | A | 5/1986 | Salo et al. |
| 4,722,342 | A | 2/1988 | Amundson |
| 4,730,619 | A | 3/1988 | Koning et al. |
| 4,791,931 | A | 12/1988 | Slate |
| 4,834,710 | A | 5/1989 | Fleck |
| 4,919,133 | A | 4/1990 | Chiang |
| 5,007,427 | A | 4/1991 | Suzuki et al. |
| 5,014,702 | A | 5/1991 | Alt |
| 5,024,222 | A | 6/1991 | Thacker |

(Continued)

FOREIGN PATENT DOCUMENTS

| | | |
|---|---|---|
| EP | 0547734 A2 | 6/1993 |
| EP | 0879618 A1 | 11/1998 |

(Continued)

OTHER PUBLICATIONS

"U.S. Appl. No. 11/682,448, Non Final Office Action mailed Aug. 13, 2012", 8 pgs.

(Continued)

*Primary Examiner* — Christopher D Koharski
*Assistant Examiner* — Roland Dinga
(74) *Attorney, Agent, or Firm* — Schwegman Lundberg & Woessner, P.A.

(57) ABSTRACT

Pacing post-conditioning (PPC) therapy is applied to a patient to minimize ischemic injury associated with MI and/or reperfusion injury associated with a post-MI revascularization procedure. In various embodiments, a PPC therapy is delivered by executing a pacing protocol with pacing parameters determined and dynamically adjusted based on patient-specific factors to ensure efficacy and safety of the patient.

20 Claims, 12 Drawing Sheets

(56) References Cited

U.S. PATENT DOCUMENTS

| | | |
|---|---|---|
| 5,058,584 A | 10/1991 | Bourgeois |
| 5,072,458 A | 12/1991 | Suzuki |
| 5,111,818 A | 5/1992 | Suzuki et al. |
| 5,135,004 A | 8/1992 | Adams et al. |
| 5,184,615 A | 2/1993 | Nappholz et al. |
| 5,199,428 A | 4/1993 | Obel et al. |
| 5,282,840 A | 2/1994 | Hudrlik et al. |
| 5,313,953 A | 5/1994 | Yomtov et al. |
| 5,360,436 A | 11/1994 | Alt et al. |
| 5,376,106 A | 12/1994 | Stahmann et al. |
| 5,391,188 A | 2/1995 | Nelson et al. |
| 5,484,419 A | 1/1996 | Fleck |
| 5,531,768 A | 7/1996 | Alferness |
| 5,588,432 A | 12/1996 | Crowley |
| 5,634,899 A | 6/1997 | Shapland et al. |
| 5,649,968 A | 7/1997 | Alt et al. |
| 5,755,671 A | 5/1998 | Albrecht et al. |
| 5,824,021 A | 10/1998 | Rise |
| 5,919,209 A | 7/1999 | Schouten |
| 6,021,350 A | 2/2000 | Mathson |
| 6,058,331 A | 5/2000 | King |
| 6,104,956 A | 8/2000 | Naritoku et al. |
| 6,108,577 A | 8/2000 | Benser |
| 6,115,628 A | 9/2000 | Stadler et al. |
| 6,208,894 B1 | 3/2001 | Schulman et al. |
| 6,233,486 B1 | 5/2001 | Ekwall et al. |
| 6,238,422 B1 | 5/2001 | Oort |
| 6,256,538 B1 | 7/2001 | Ekwall |
| 6,272,379 B1 | 8/2001 | Fischell et al. |
| 6,278,894 B1 | 8/2001 | Salo et al. |
| 6,285,907 B1 | 9/2001 | Kramer et al. |
| 6,314,323 B1 | 11/2001 | Ekwall |
| 6,368,284 B1 | 4/2002 | Bardy |
| 6,408,208 B1 | 6/2002 | Sun |
| 6,411,845 B1 | 6/2002 | Mower |
| 6,445,953 B1 | 9/2002 | Bulkes et al. |
| 6,477,402 B1 | 11/2002 | Lynch et al. |
| 6,501,983 B1 | 12/2002 | Natarajan et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,610,713 B2 | 8/2003 | Tracey |
| 6,628,988 B2 | 9/2003 | Kramer et al. |
| 6,711,436 B1 | 3/2004 | Duhaylongsod |
| 6,735,479 B2 | 5/2004 | Fabian et al. |
| 6,763,267 B2 | 7/2004 | Ding |
| 6,813,516 B2 | 11/2004 | Ujhelyi et al. |
| 6,827,690 B2 | 12/2004 | Bardy |
| 6,838,471 B2 | 1/2005 | Tracey |
| 6,842,642 B2 | 1/2005 | Vanhout |
| 6,845,267 B2 | 1/2005 | Harrison et al. |
| 6,865,420 B1 | 3/2005 | Kroll |
| 6,892,095 B2 | 5/2005 | Salo |
| 6,907,285 B2 | 6/2005 | Denker et al. |
| 6,913,577 B2 | 7/2005 | Bardy |
| 6,937,899 B2 | 8/2005 | Sheldon et al. |
| 6,950,701 B2 | 9/2005 | Begemann et al. |
| 6,965,797 B2 | 11/2005 | Pastore et al. |
| 6,973,349 B2 | 12/2005 | Salo |
| 7,010,345 B2 | 3/2006 | Hill et al. |
| 7,025,730 B2 | 4/2006 | Cho et al. |
| 7,039,462 B2 | 5/2006 | Pastore et al. |
| 7,043,305 B2 | 5/2006 | KenKnight et al. |
| 7,062,314 B2 | 6/2006 | Zhu et al. |
| 7,062,325 B1 | 6/2006 | Krig et al. |
| 7,069,070 B2 | 6/2006 | Carlson et al. |
| 7,072,711 B2 | 7/2006 | Girouard et al. |
| 7,092,755 B2 | 8/2006 | Florio |
| 7,158,832 B2 | 1/2007 | Kieval et al. |
| 7,171,258 B2 | 1/2007 | Goode |
| 7,215,992 B2 | 5/2007 | Stahmann et al. |
| 7,215,997 B2 | 5/2007 | Yu et al. |
| 7,277,761 B2 | 10/2007 | Shelchuk |
| 7,295,874 B2 | 11/2007 | Prinzen et al. |
| 7,299,087 B2 | 11/2007 | Bardy |
| 7,333,854 B1 | 2/2008 | Brewer et al. |
| 7,340,303 B2 | 3/2008 | Zhu |
| 7,364,547 B2 | 4/2008 | Stahmann et al. |
| 7,366,568 B2 | 4/2008 | Pastore et al. |
| 7,437,191 B2 | 10/2008 | Pastore et al. |
| 7,450,988 B2 | 11/2008 | Ross et al. |
| 7,460,906 B2 | 12/2008 | Libbus |
| 7,479,112 B2 | 1/2009 | Sweeney et al. |
| 7,486,991 B2 | 2/2009 | Libbus et al. |
| 7,668,594 B2 | 2/2010 | Brockway et al. |
| 7,711,420 B2 | 5/2010 | Baynham et al. |
| 8,412,326 B2 | 4/2013 | Arcot-Krishnamurthy et al. |
| 8,615,296 B2 | 12/2013 | Pastore et al. |
| 2002/0026222 A1 | 2/2002 | Schauerte et al. |
| 2002/0042632 A1 | 4/2002 | Iaizzo et al. |
| 2002/0072776 A1 | 6/2002 | Osorio et al. |
| 2002/0072777 A1 | 6/2002 | Lu |
| 2002/0082660 A1 | 6/2002 | Stahmann et al. |
| 2002/0091415 A1 | 7/2002 | Lovett et al. |
| 2002/0123772 A1 | 9/2002 | Sun et al. |
| 2002/0128563 A1 | 9/2002 | Carlson et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0055461 A1 | 3/2003 | Girouard et al. |
| 2003/0060854 A1 | 3/2003 | Zhu |
| 2003/0105493 A1 | 6/2003 | Salo |
| 2003/0120313 A1 | 6/2003 | Begemann et al. |
| 2003/0120315 A1 | 6/2003 | Spinelli et al. |
| 2003/0139778 A1 | 7/2003 | Fischell et al. |
| 2003/0158492 A1 | 8/2003 | Sheldon et al. |
| 2003/0158584 A1 | 8/2003 | Cates et al. |
| 2003/0199956 A1 | 10/2003 | Struble et al. |
| 2003/0204206 A1 | 10/2003 | Padua et al. |
| 2003/0204231 A1 | 10/2003 | Hine et al. |
| 2003/0229380 A1 | 12/2003 | Adams et al. |
| 2003/0233130 A1 | 12/2003 | Padmanabhan et al. |
| 2004/0015081 A1 | 1/2004 | Kramer et al. |
| 2004/0038947 A1 | 2/2004 | Wink et al. |
| 2004/0049235 A1 | 3/2004 | Deno et al. |
| 2004/0088015 A1 | 5/2004 | Casavant et al. |
| 2004/0088017 A1 | 5/2004 | Sharma et al. |
| 2004/0102815 A1 | 5/2004 | Balczewski et al. |
| 2004/0106960 A1* | 6/2004 | Siejko et al. .................. 607/17 |
| 2004/0106961 A1 | 6/2004 | Siejko et al. |
| 2004/0133247 A1 | 7/2004 | Stahmann et al. |
| 2004/0138719 A1 | 7/2004 | Cho et al. |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0065568 A1 | 3/2005 | Liu et al. |
| 2005/0075673 A1 | 4/2005 | Warkentin et al. |
| 2005/0090719 A1 | 4/2005 | Scheiner et al. |
| 2005/0096705 A1 | 5/2005 | Pastore et al. |
| 2005/0096706 A1 | 5/2005 | Salo |
| 2005/0131467 A1 | 6/2005 | Boveja |
| 2005/0137631 A1 | 6/2005 | Yu et al. |
| 2005/0143779 A1 | 6/2005 | Libbus |
| 2005/0143780 A1 | 6/2005 | Henry et al. |
| 2005/0149126 A1 | 7/2005 | Libbus |
| 2005/0149127 A1 | 7/2005 | Libbus |
| 2005/0149129 A1 | 7/2005 | Libbus et al. |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2005/0283195 A1 | 12/2005 | Pastore et al. |
| 2005/0288721 A1 | 12/2005 | Girouard et al. |
| 2006/0020294 A1 | 1/2006 | Brockway et al. |
| 2006/0030892 A1 | 2/2006 | Kadhiresan et al. |
| 2006/0116593 A1 | 6/2006 | Zhang et al. |
| 2006/0136049 A1 | 6/2006 | Rojo |
| 2006/0149326 A1 | 7/2006 | Prinzen et al. |
| 2006/0195038 A1 | 8/2006 | Carlson et al. |
| 2006/0206158 A1 | 9/2006 | Wu et al. |
| 2006/0241357 A1 | 10/2006 | Chirife |
| 2006/0241704 A1 | 10/2006 | Shuros et al. |
| 2006/0247686 A1 | 11/2006 | Girouard et al. |

(56) References Cited

U.S. PATENT DOCUMENTS

| | | |
|---|---|---|
| 2006/0247700 A1 | 11/2006 | Jackson |
| 2006/0247702 A1 | 11/2006 | Stegemann et al. |
| 2006/0253156 A1 | 11/2006 | Pastore et al. |
| 2006/0259087 A1 | 11/2006 | Baynham et al. |
| 2006/0259088 A1 | 11/2006 | Pastore et al. |
| 2006/0271119 A1 | 11/2006 | Ni et al. |
| 2006/0282000 A1 | 12/2006 | Zhang et al. |
| 2006/0287684 A1 | 12/2006 | Baynham et al. |
| 2007/0021789 A1 | 1/2007 | Pastore et al. |
| 2007/0021790 A1 | 1/2007 | Kieval et al. |
| 2007/0021798 A1 | 1/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0043393 A1 | 2/2007 | Brockway et al. |
| 2007/0049835 A1 | 3/2007 | Goode |
| 2007/0054871 A1 | 3/2007 | Pastore et al. |
| 2007/0060972 A1 | 3/2007 | Kieval et al. |
| 2007/0142864 A1 | 6/2007 | Libbus et al. |
| 2007/0142871 A1 | 6/2007 | Libbus et al. |
| 2007/0150005 A1 | 6/2007 | Sih et al. |
| 2007/0150015 A1 | 6/2007 | Zhang et al. |
| 2007/0162081 A1 | 7/2007 | Yu et al. |
| 2007/0167984 A1 | 7/2007 | Kieval et al. |
| 2007/0179392 A1 | 8/2007 | Zhang |
| 2007/0191892 A1 | 8/2007 | Mullen et al. |
| 2007/0233192 A1 | 10/2007 | Craig |
| 2007/0239218 A1 | 10/2007 | Carlson et al. |
| 2007/0282380 A1 | 12/2007 | Brooke et al. |
| 2007/0299356 A1 | 12/2007 | Wariar et al. |
| 2008/0004669 A1 | 1/2008 | Sathaye et al. |
| 2008/0015659 A1 | 1/2008 | Zhang et al. |
| 2008/0021507 A1 | 1/2008 | Libbus et al. |
| 2008/0027495 A1 | 1/2008 | Prinzen et al. |
| 2008/0058661 A1 | 3/2008 | Bardy |
| 2008/0058881 A1 | 3/2008 | Wagner et al. |
| 2008/0071315 A1 | 3/2008 | Baynham et al. |
| 2008/0081354 A1 | 4/2008 | Qu et al. |
| 2008/0082135 A1 | 4/2008 | Arcot-Krishnamurthy et al. |
| 2008/0091138 A1 | 4/2008 | Pastore et al. |
| 2008/0132972 A1 | 6/2008 | Shuros et al. |
| 2008/0140141 A1 | 6/2008 | Ben-David et al. |
| 2008/0167694 A1 | 7/2008 | Bolea et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2008/0215105 A1 | 9/2008 | Pastore et al. |
| 2008/0221636 A1 | 9/2008 | Pastore et al. |
| 2008/0234774 A1 | 9/2008 | Baynham et al. |
| 2009/0025459 A1 | 1/2009 | Zhang et al. |
| 2009/0048641 A1 | 2/2009 | Libbus |
| 2009/0082781 A1 | 3/2009 | Tran et al. |
| 2009/0124916 A1 | 5/2009 | Sweeney et al. |
| 2009/0192560 A1 | 7/2009 | Arcot-Krishnamurthy et al. |
| 2009/0234401 A1 | 9/2009 | Zielinski et al. |
| 2009/0281591 A1 | 11/2009 | Shuros et al. |
| 2009/0318984 A1* | 12/2009 | Mokelke et al. .................. 607/4 |
| 2010/0016913 A1 | 1/2010 | Arcot-Krishnamurthy et al. |
| 2010/0016916 A1 | 1/2010 | Arcot-Krishnamurthy et al. |
| 2010/0130913 A1 | 5/2010 | Baynham et al. |
| 2010/0305648 A1 | 12/2010 | Arcot-Krishnamurthy et al. |
| 2011/0106197 A1 | 5/2011 | Arcot-Krishnamurthy et al. |

FOREIGN PATENT DOCUMENTS

| | | |
|---|---|---|
| EP | 2000078391 A1 | 12/2000 |
| EP | 1437159 A1 | 7/2004 |
| EP | 1690566 A1 | 8/2006 |
| JP | 10-263093 A | 10/1998 |
| JP | 2005-538776 A | 12/2005 |
| WO | WO-9302745 A1 | 2/1993 |
| WO | WO-9518649 A1 | 7/1995 |
| WO | WO-00/78391 A1 | 12/2000 |
| WO | WO-0078391 A1 | 12/2000 |
| WO | WO-0115609 A1 | 3/2001 |
| WO | WO-0124876 A1 | 4/2001 |
| WO | WO-0128625 | 4/2001 |
| WO | WO-0176689 A2 | 10/2001 |
| WO | WO-03082080 A2 | 10/2003 |
| WO | WO-2004024229 A1 | 3/2004 |
| WO | WO-2004058326 A2 | 7/2004 |
| WO | WO-2005042091 A1 | 5/2005 |
| WO | WO-2005-113066 A1 | 12/2005 |
| WO | WO-2006074189 A1 | 7/2006 |
| WO | WO-2006079010 A1 | 7/2006 |
| WO | WO-2006105474 A2 | 10/2006 |
| WO | WO-2006115693 A2 | 11/2006 |
| WO | WO-2006115693 A3 | 11/2006 |
| WO | WO-2006121842 A2 | 11/2006 |
| WO | WO-2006124636 A2 | 11/2006 |
| WO | WO-2006124729 A2 | 11/2006 |
| WO | WO-2007078410 A1 | 7/2007 |
| WO | WO-2007133962 A2 | 11/2007 |
| WO | WO-2008063396 A1 | 5/2008 |
| WO | WO-2008109040 A2 | 9/2008 |
| WO | WO-2008109040 A3 | 9/2008 |
| WO | WO-2008115514 A1 | 9/2008 |
| WO | WO-2009114081 A1 | 9/2009 |
| WO | WO-2011/053369 A1 | 5/2011 |

OTHER PUBLICATIONS

"U.S. Appl. No. 12/709,867, Response filed Aug. 21, 2012 to Non Final Office Action mailed Apr. 30, 2012", 15 pgs.

"U.S. Appl. No. 12/709,867, Non Final Office Action mailed Apr. 30, 2012", 15 pgs.

"Chinese Application Serial No. 200880007463.3, Response filed Jul. 23, 2012 to Office Action mailed Mar. 14, 2012", (English Translation of Amended Claims), 5 pgs.

"European Application Serial No. 08726356.2, Examination Notification Art 94(3) mailed Aug. 22, 2012", 5 pgs.

"International Application Serial No. PCT/US2010/024930, International Preliminary Report on Patentability mailed May 10, 2012", 9 pgs.

"Japanese Application Serial No. 2009-552705, Office Action mailed Apr. 19, 2012", (w/ English Translation), 7 pgs.

"Japanese Application Serial No. 2012-536798 , Voluntary Amendment filed May 31, 2012", 7 pgs.

"U.S. Appl. No. 11/682,448, Final Office Action mailed Dec. 8, 2011", 10 pgs.

"U.S. Appl. No. 11/682,448, Response filed Mar. 6, 2012 to Final Office Action mailed Dec. 8, 2011", 14 pgs.

"U.S. Appl. No. 11/682,448, Response filed Sep. 23, 2011 to Non Final Office Action mailed Jun. 23, 2011", 13 pgs.

"Chinese Application Serial No. 200880007463.3, Office Action mailed Mar. 6, 2012", (w/ English Translation), 21 pgs.

"Japanese Application Serial No. 2009-552705, Office Action mailed Dec. 6, 2011", (w/ English Translation), 12 pgs.

"Japanese Application No. 2009-552705, Response filed Mar. 6, 2012 to Office Action mailed Dec. 6, 2011", (w/ English Translation of Amended Claims), 11 pgs.

"Japanese Application Serial No. 2009-554560, Office Action mailed Jan. 10, 2012", (w/ English Translation), 5 pgs.

"Japanese Application No. 2009-554560, Response filed Apr. 10, 2012 to Office Action mailed Jan. 10, 2012", (w/ English Translation of Amended Claims), 12 pgs.

"U.S. Appl. No. 11/682,448, Final Office Action mailed Oct. 7, 2010", 6 pgs.

"U.S. Appl. No. 11/682,448, Advisory Action mailed Feb. 4, 2011", 5 pgs.

"U.S. Appl. No. 11/682,448, Non Final Office Action mailed Jun. 23, 2011", 8 pgs.

"U.S. Appl. No. 11/682,448, Response filed Jan. 7, 2011 to Final Office Action mailed Oct. 7, 2010", 14 pgs.

"U.S. Appl. No. 11/682,448, Response filed Feb. 7, 2011 to Final Office Action mailed Oct. 7, 2010 and Advisory Action mailed Feb. 4, 2011", 15 pgs.

(56) References Cited

OTHER PUBLICATIONS

"Australian Application Serial No. 2008-223498, Response filed May 25, 2011 to First Examiner Report mailed Aug. 16, 2010", 21 pgs.
"Japanese Application Serial No. 2009-552705, Amendment filed Oct. 21, 2009", (w/ English Translation), 43 pgs.
"U.S. Appl. No. 11/682,448, Non-Final Office Action mailed Apr. 5, 2010", 16 pgs.
"U.S. Appl. No. 11/682,448, Response filed Jul. 1, 2010 to Non Final Office Action mailed Apr. 5, 2010", 12 pgs.
"U.S. Appl. No. 11/687,957, Notice of Allowance mailed Dec. 21, 2009", 8 pgs.
"U.S. Appl. No. 11/687,957, Non-Final Office Action mailed Mar. 6, 2009", 7 pgs.
"U.S. Appl. No. 11/687,957, Response filed Aug. 6, 2009 to Non-Final Office Action mailed Mar. 6, 2009", 17 pgs.
"Australian Application No. 2008223498, First Examiner Report mailed Aug. 16, 2010", 3 Pgs.
"European Application No. 08726356.2, Office Action mailed May 31, 2010", 7 Pgs.
"European Application No. 08726356.2, Response filed Aug. 27, 2010 to Communication dated May 31, 2010", 14 pgs.
"International Application No. PCT/US2008/003594, International Search Report mailed Jul. 9, 2008", 5 pgs.
"International Application No. PCT/US2008/003594, Written Opinion mailed Jul. 9, 2008", 6 pgs.
"International Application No. PCT//US2010/024930, Search Report mailed Jun. 2, 2010", 4 pgs.
"International Application No. PCT//US2010/024930, Written Opinion mailed Jun. 2, 2010", 8 pgs.
"International Application Serial No. PCT/US2008/002799, International Search Report mailed Oct. 15, 2008", 6 pgs.
"International Application Serial No. PCT/US2008/002799, Invitation to Pay Fees and Partial International Search Report mailed Jul. 14, 2008", 7 pgs.
"International Application Serial No. PCT/US2008/002799, Written Opinion mailed Oct. 15, 2008", 11 pgs.
"International Application Serial No. PCT/US2008/002799. PCT Search Report", 6 pgs.
Airaksinen, K. E., et al., "Antiarrhythmic effect of repeated coronary occlusion during balloon angioplasty", J Am Coll Cardiol., 29(5), (Apr. 1997), 1035-1038.
Amende, I., "Hemodynamics in ischemia: diastolic phase", Z. Kardiol., 73 Suppl 2, [Article in German With English Abstract], (1984), 127-33.
Andersen, H, et al., "Long-term follow-up of patients from a randomised trial of atrial versus ventricular pacing for sick-sinus syndrome", Lancet, 350(9086), (Oct. 25, 1997), 1210-6.
Benchimol, A, et al., "Cardiac hemodynamics during stimulation of the right atrium, right ventricle, and left ventricle in normal and abnormal hearts", Circulation, 33(6), (Jun. 1966), 933-44.
Dzwonczyk, R., et al., "Myocardial electrical impedance responds to ischemia and reperfusion in humans", IEEE Transactions on Biomedical Engineering, 51(12), (Dec. 2004), 2206-2209.
Girouard, Steven D., "Pulmonary Vein Stent for Treating Atrial Fibrillation", U.S. Appl. No. 60/298,741, filed Jun. 15, 2001, 14 pgs.
Grassi, Guido, et al., "Baroreflex and non-baroreflex modulation of vagal cardiac control after myocardial infarction", Am J Cardiol., 84(5), (Sep. 1, 1999), 525-9.
Henriques, Jose P., et al., "Outcome of primary angioplasty for acute myocardial infarction during routine duty hours versus during off-hours", J Am Coll Cardiol, 41(12), (Jun. 18, 2003), 2138-2142.
Ishihara, M., et al., "Implications of prodromal angina pectoris in anterior wall acute myocardial infarction: acute angiographic findings and long-term prognosis", J Am Coll Cardiol., 30(4), (1997), 970-5.
Kin, Hajime, et al., "Postconditioning attenuates myocardial ischemia-reperfusion injury by inhibiting events in the early minutes of reperfusion", Cardiovascular Research, 62(1), (Apr. 1, 2004), 74-85.
Kis, A., "Repeated cardiac pacing extends the time during which canine hearts are protected against ischaemia-induced arrhythmias : role of nitric oxide.", Journal of Molecular and Cellular Cardiology, 31(6), (Jun. 1999), 1229-1241.
Kloner, R. A., et al., "Prospective temporal analysis of the onset of preinfarction angina versus outcome: an ancillary study in TIMI-9B", Circulation, 97(11), (1998), 1042-5.
Koning, M M, "Rapid ventricular pacing produces myocardial protection by nonischemic activation of KATP+ channels", Circulation, 93(1), (Jan. 1, 1996), 178-186.
Krayenbuhl, H. P., "Hemodynamics in ischemia. Systolic phase", Z. Kardiol., 73 Suppl 2, [Article in German with English Abstract], (1984), 119-25.
Leclercq, C, et al., "Hemodynamic importance of preserving the normal sequence of ventricular activation in permanent cardiac pacing", Am Heart J., 129(6), (Jun. 1995), 1133-41.
Loukogeorgakis, S. P., et al., "Remote ischemic preconditioning provides early and late protection against endothelial ischemia-reperfusion injury in humans: role of the autonomic nervous system.", J Am Coll Cardiol., 46(3), (Aug. 2, 2005), 450-6.
Makhoul, John, "Linear Prediction: A Tutorial Review", Proceedings of the IEEE, 63, (Apr. 1975), 561-580.
Meier, B., et al., "Coronary Pacing During Percutaneous Transluminal Coronary Angioplasty", Circulation, 71(3), (Mar. 1985), 557-561.
Murry, C. E., et al., "Preconditioning with ischemia: a delay of lethal cell injury in ischemic myocardium", Circulation, 74(5), (1986), 1124-1136.
Ovize, M., et al., "Stretch preconditions canine myocardium.", Am J Physiol., 266(1 Pt 2), (Jan. 1994), H137-46.
Panju, Akbar A, et al., "Is This Patient Having a Myocardial Infraction?", JAMA, 280(14), (Oct. 14, 1996), 1256-1263.
Prinzen, F. W., et al., "Relation between the pacing induced sequence of activation and left ventricular pump function in animals.", Pacing Clin Electrophysiol., 25(4 Pt 1), (Apr. 2002), 484-98.
Prinzen, Frits W, "Mapping of regional myocardial strain and work during ventricular pacing: experimental study using magnetic resonance imaging tagging", Journal of the American College of Cardiology, 33(6), (May 1999), 1735-1742.
Rosa, A., et al., "Ectopic Pacing at Physiological Rate Improves Postanoxic Recovery of the Developing Heart", Am. J. Physiol.—Heart Circ. Physiol., 284, (2003), H2384-H2392.
Rosenqvist, M, et al., "The effect of ventricular activation sequence on cardiac performance during pacing", Pacing and Electrophysiology, 19(9), (1996), 1279-1286.
Salerno, D. M., "Seismocardiography for monitoring changes in left ventricular function during ischemia.", Chest, 100(4), (Oct. 1991), 991-3.
Solomon, S. D., et al., "Angina pectoris prior to myocardial infarction protects against subsequent left ventricular remodeling", J Am Coll Cardiol., 43(9), (2004), 1511-4.
Tavel, Morton E, "The Appearance of Gallop Rhythm after Exercise Stress Testing", Clin. Cardiol., vol. 19, (1996), 887-891.
Tsang, A., et al., "Postconditioning: a form of "modified reperfusion" protects the myocardium by activating the phosphatidylinositol 3-kinase-Akt pathway", Circ Res., 95(3), Epub Jul. 8, 2004, (Aug. 6, 2004), 230-2.
Vanagt, W. Y., et al., "Pacing-induced dys-synchrony preconditions rabbit myocardium against ischemia/reperfusion injury.", Circulation, 114(1 Suppl), (Jul. 4, 2006), I264-I269.
Vanagt, W. Y. R., et al., "Ventricular Pacing for Improving Myocardial Tolerance to Ischemic", Progress Report on Project Guidant-CARIM, (Oct. 2003), 1-25.
Vegh, A, et al., "Transient ischaemia induced by rapid cardiac pacing results in myocardial preconditioning", Cardiovascular Research, 25(12), (Dec. 1991), 1051-3.
Wu, Zhong-Kai, et al., "Ischemic preconditioning suppresses ventricular tachyarrhythmias after myocardial revascularization", Circulation, 106(24), (Dec. 10, 2002), 3091-3096.
Yang, S. M., et al., "Multiple, brief coronary occlusions during early reperfusion protect rabbit hearts by targeting cell signaling pathways", Journal of the American College of Cardiology, 44(5), (Sep. 1, 2004), 1103-1110.

(56) References Cited

OTHER PUBLICATIONS

Zhao, Zhi-Qing, et al., "Inhibition of myocardial injury by ischemic postconditioning during reperfusion: comparison with ischemic preconditioning", Am J Physiol Heart Circ Physiol, 285(2), (Aug. 2003), H579-H588.

"U.S. Appl. No. 11/682,448, Advisory Action mailed Mar. 25, 2013", 4 pgs.

"U.S. Appl. No. 11/682,448, Final Office Action mailed Jan. 16, 2013", 9 pgs.

"U.S. Appl. No. 11/682,448, Notice of Allowance mailed Aug. 20, 2013", 6 pgs.

"U.S. Appl. No. 11/682,448, Response filed Mar. 4, 2013 to Final Office Action mailed Jan. 16, 2013", 13 pgs.

"U.S. Appl. No. 11/682,448, Response filed May 14, 2013 to Final Office Action mailed Jan. 16, 2013", 12 pgs.

"U.S. Appl. No. 11/682,448, Response filed Nov. 13, 2012 to Non-Final Office Action mailed Aug. 13, 2012", 13 pgs.

"U.S. Appl. No. 12/709,867, Notice of Allowance mailed Dec. 3, 2012", 5 pgs.

"U.S. Appl. No. 12/770,351, Advisory Action mailed Oct. 30, 2013", 3 pgs.

"U.S. Appl. No. 12/770,351, Final Office Action mailed Jun. 11, 2013", 14 pgs.

"U.S. Appl. No. 12/770,351, Non Final Office Action mailed Oct. 11, 2012", 13 pgs.

"U.S. Appl. No. 12/770,351, Response filed Jan. 9, 2013 to Non Final Office Action mailed Oct. 11, 2012", 12 pgs.

"U.S. Appl. No. 12/770,351, Response filed Aug. 8, 2013 to Final Office Action mailed Jun. 11, 2013", 13 pgs.

"European Application Serial No. 08726356.2, Response filed Dec. 19, 2012 to Examination Notification Art. 94(3) mailed Aug. 22, 2012", 14 pgs.

"Japanese Application Serial No. 2012-536798, Office Action mailed Jul. 16, 2013", With English Translation, 6 pgs.

"Japanese Application Serial No. 2012-536798, Response filed Oct. 9, 2013 to Non Final Office Action dated Jul. 16, 2013", With English Claims, 15 pgs.

\* cited by examiner

METHOD AND APPARATUS FOR AUTOMATED CONTROL OF PACING POST-CONDITIONING

CLAIM OF PRIORITY

This application claims the benefit of provisional U.S. patent application Ser. No. 61/245,067, filed on Sep. 23, 2009, which is hereby incorporated by reference in its entirety.

TECHNICAL FIELD

This document relates generally to cardiac pacing systems and particularly to a system for delivering pacing post-conditioning (PPC) therapy for myocardium protection with automated control of pacing parameters.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium (cardiac muscles). In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions. A blocked or otherwise abnormal electrical conduction and/or deteriorated myocardial tissue cause dyssynchronous contraction of the heart, resulting in poor hemodynamic performance, including a diminished blood supply to the heart and the rest of the body. The condition in which the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen supply and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure.

When a blood vessel such as the coronary artery is partially or completely occluded, a revascularization procedure such as percutaneous transluminal coronary angioplasty (PTCA) can be performed to reopen the occluded blood vessel. However, the revascularization procedure itself involves a temporary occlusion of the coronary artery. Reperfusion that follows the reopening of the occluded blood vessel is also known to cause cardiac injury, known as reperfusion injury. In addition, plaques dislodged and displaced by the revascularization procedure may enter small blood vessels branching from the blood vessel in which the revascularization is performed, causing occlusion of these small blood vessels. The revascularization procedure may also cause distal embolization, i.e., obstruction of the artery caused by the plaque dislodged during the procedure. Therefore, there is a need for minimizing cardiac injury associated with MI and the subsequent revascularization procedure.

SUMMARY

Pacing post-conditioning (PPC) therapy is applied to a patient to minimize ischemic injury associated with MI and/or reperfusion injury associated with a post-MI revascularization procedure. In various embodiments, a PPC therapy is delivered by executing a pacing protocol with pacing parameters determined and dynamically adjusted based on patient-specific factors to ensure efficacy and safety of the patient.

In one embodiment, a cardiac pacing system includes a pacing output circuit, a storage device, one or more PPC protocols, and a pacing control circuit. The pacing output circuit delivers pacing pulses. The one or more PPC protocols are stored in the storage device and each specify a pacing sequence including alternating non-pacing and pacing periods. The non-pacing periods each include a non-pacing duration during which no pacing pulse is timed to be delivered. The pacing periods each include a pacing duration during which a plurality of pacing pulses is timed to be delivered according to a stress augmentation pacing mode adapted to augment myocardial mechanical stress to a level effecting cardioprotection against myocardial injury. The pacing control circuit is programmed to execute a current pacing protocol and includes a parameter input and a protocol generator. The parameter input receives one or more protocol generation parameters including at least one or more physiological parameters. The protocol generator is programmed to generate the current pacing protocol using the one or more PPC protocols and the one or more protocol generation parameters. The current pacing protocol specifies a plurality of pacing parameters. The one or more protocol generation parameters are used to calculate one or more pacing parameters of the plurality of pacing parameters.

In one embodiment, a method for cardiac pacing is provided. At least one PPC protocol is received from a storage device that stores one or more PPC protocols each specifying a pacing sequence. The pacing sequence includes alternating non-pacing and pacing periods. The non-pacing periods each include a non-pacing duration during which no pacing pulse is timed to be delivered. The pacing periods each include a pacing duration during which a plurality of pacing pulses is timed to be delivered according to a stress augmentation pacing mode adapted to augment myocardial mechanical stress to a level effecting cardioprotection against myocardial injury. One or more protocol generation parameters including at least one or more physiological parameters are received. A current pacing protocol specifying a plurality of pacing parameters is generated using the at least one PPC protocol and the one or more protocol generation parameters. Delivery of pacing pulses from a cardiac pacemaker is controlled by executing the current pacing protocol.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
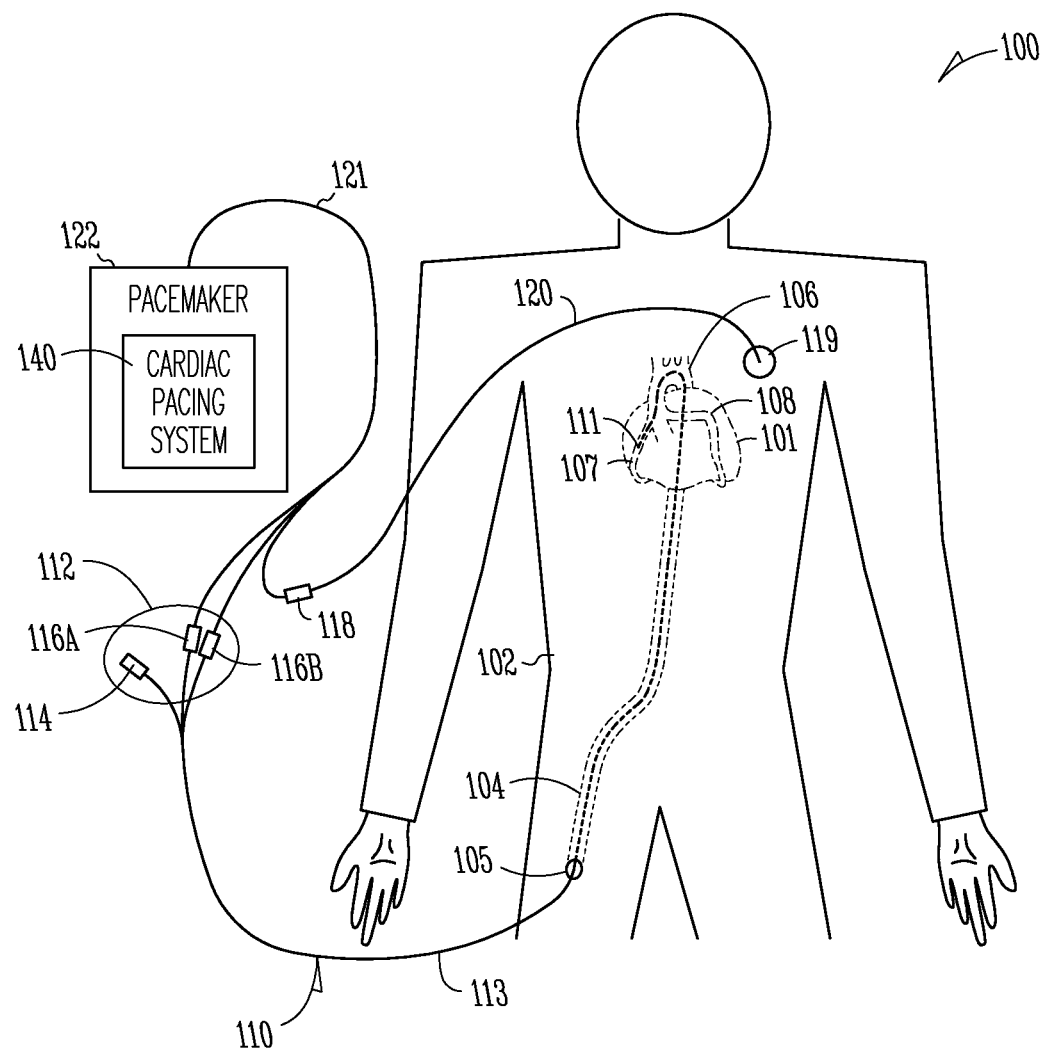
FIG. 1 is an illustration of an embodiment of a system providing for pacing during revascularization and portions of an environment in which the system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

In this document, "revascularization" includes reopening of a completely or partially occluded blood vessel using percutaneous transluminal vascular intervention (PTVI) procedure, such as a percutaneous transluminal coronary angioplasty (PTCA) procedure performed in response to cardiac ischemia or myocardial infarction (MI), using PTVI devices such as those discussed in this document. A "user" includes a physician or other caregiver who treats a patient using the method and apparatus discussed in this document.

This document discusses a pacing system that delivers pacing pulses to a patient after MI. In an application, the pacing system provides for pacing post-conditioning (PPC) therapy during the revascularization procedure. The PPC is an acute pacing cardioprotection therapy that includes the delivery of pacing pulses after the temporary occlusion of a coronary artery to prevent and/or reduce cardiac injury associated with MI and the subsequent revascularization procedure. The pacing system is capable of delivering the PPC therapy without substantially interfering with the revascularization procedure. In various applications, the pacing system provides for acute pacing cardioprotection therapy before, during, and after the occlusion of the coronary artery associated with MI and the subsequent revascularization procedure.

To deliver pacing pulses during the revascularization procedure, one or more pacing electrodes are incorporated onto the one or more PTVI devices. Examples of such PTVI devices include guide wires, guide catheters, and angioplasty catheters such as dilatation balloon catheters, stent delivery systems, brachytherapy devices, atherectomy devices, and distal embolization protection devices. A pacemaker connected to the one or more PTVI devices generates the pacing pulses and controls the delivery of the acute pacing cardioprotection therapy by automatically executing a pacing protocol. In one embodiment, the pacing protocol is a PPC protocol specifying a pacing sequence including alternating non-pacing and pacing periods. In various embodiments, the pacing parameters used in the PPC protocol are determined empirically and/or adjusted using parameters measured from the patient receiving the PPC therapy.

FIG. 1 is an illustration of an embodiment of a system 100 providing for pacing during revascularization and portions of an environment in which system 100 is used. System 100 includes a PTVI device 110, a pacemaker 122, and a cable 121 connecting PTVI device 110 and pacemaker 122. When needed, system 100 also includes a reference electrode 119, which is a surface electrode, such as a skin patch electrode, connected to a lead 120. Lead 120 is connected to a connector 118 allowing its connection to cable 121.

PTVI device 110 is used during a revascularization procedure and includes a distal end portion 111 for intravascular placement, a proximal end portion 112, and an elongate body 113 coupled between distal end portion 111 and proximal end portion 112. Proximal end portion 112 includes a proximal end device 114 and pacing connectors 116A-B. Proximal end device 114 includes various connectors and other structures allowing manipulation of PTVI device 110 including the percutaneous transluminal insertion of the device and operation of an angioplasty device at distal end 111. Pacing connectors 116A-B provide for electrical connections between pacemaker 122 and PTVI device 110 through cable 121. In the illustrated embodiment, PTVI device 110 is a PTCA device used in a PTCA procedure. During the PTCA procedure, an opening 105 is made on a femoral artery 104 in a patient's body 102. PTVI device 110 is inserted into femoral artery 104 and advanced to an aorta 106 and then to a right coronary artery 107, which is narrowed or blocked. The angioplasty device at distal end 111 is then used to open up the blocked right coronary artery 107. In another embodiment, PTVI device 110 is used to open up a blocked left coronary artery 108.

Distal end portion 111 of PTVI device 110 includes one or more pacing electrodes to allow pacing pulses to be delivered to a heart 101 during the PTCA procedure. In one embodiment, pacing pulses are delivered through two pacing electrodes on distal end portion 111 of PTVI device 110. In another embodiment, pacing pulses are delivered through a pacing electrode on distal end portion 111 of PTVI device 110 and surface electrode 119 functioning as the return electrode for pacing.

Pacemaker 122 delivers pacing pulses by executing a cardioprotective pacing protocol. In one embodiment, the cardioprotective pacing protocol specifies a cardioprotective pacing sequence for preventing arrhythmias and cardiac injuries associated with the revascularization procedure. In one embodiment, pacemaker 122 is an external pacemaker such as a PSA. In another embodiment, pacemaker 122 includes an implantable pacemaker adapted for external use. Pacemaker 122 includes a cardiac pacing system 140 that provides for pacing cardioprotection therapy with automated control of therapy delivery. One or more cardioprotective pacing protocols stored in system 140 each specify a pacing sequence for augmenting mechanical stress on the myocardium of heart 101 to a level effecting cardioprotection against myocardial injury. To deliver a cardioprotective pacing therapy to a patient, system 140 receives one or more physiological parameters measured from the patient and generates a current pacing protocol specifying a plurality of pacing parameters using the one or more cardioprotective pacing protocols and the one or more physiological parameters. Delivery of the pacing cardioprotection therapy is automatically controlled by executing the current pacing protocol. In various embodiments, system 140 is used to deliver PPC therapy during revascularization.

It is to be understood that FIG. 1 is for illustrative, but not restrictive, purposes. For example, the physical structure of proximal end portion 112 depends on functional and ease-of-use considerations. Proximal end device 114 represents a structure that accommodates all the mechanical connection and access requirements, which depend on the specific configuration and function of PTVI device 110. In one embodiment, proximal end device 114 includes an integrated device as illustrated in FIG. 1. In another embodiment, proximal end device 114 branches out into multiple connectors and/or other devices. Pacing connectors 116A-B represent a structure that accommodates all the electrical connections required for delivering pacing pulses from pacemaker 122 to PTVI device 110. The number of pacing connectors depends on the number of pacing electrodes incorporated onto PTVI device 110 and how it is to be connected to cable 121. In one embodiment, when more than one electrical connection is needed for delivering the pacing pulses, proximal end portion 112 includes branched-out pacing connectors such as pacing connectors 116A-B as illustrated in FIG. 1. In another embodiment, proximal end portion 112 includes a single connector providing for multiple, independent electrical connections.

Pacemaker

Figure 2:
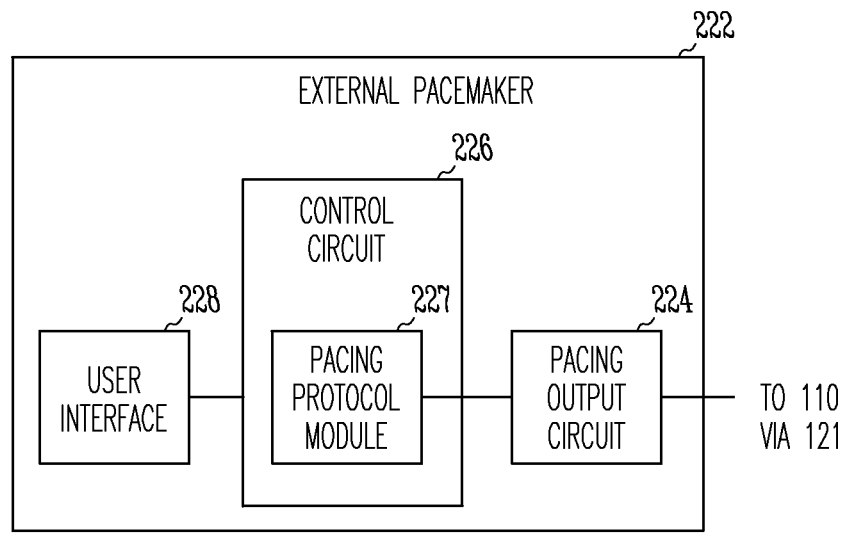
FIG. 2 is a block diagram illustrating an embodiment of a pacemaker providing for pacing during revascularization.

FIG. 2 is a block diagram illustrating an embodiment of an external pacemaker 222 that provides for pacing during revascularization. External pacemaker 222 is an embodiment of pacemaker 122 and includes a pacing output circuit 224, a user interface 228, and a control circuit 226. Pacing output circuit 224 delivers pacing pulses to PTVI device 110 through cable 121. User interface 228 allows a user to control the delivery of the pacing pulses by controlling pacing parameters and/or timing of the delivery. Control circuit 226 controls the delivery of the pacing pulses. In one embodiment, external pacemaker 222 is a PSA including a chassis that houses pacing output circuit 224 and control circuit 226. User interface 228 is incorporated onto the chassis.

In the illustrated embodiment, control circuit 226 includes a pacing protocol module 227, which enables control circuit 226 to control the delivery of the pacing pulses by automatically executing a pacing protocol. To provide an acute pacing cardioprotection therapy, the pacing protocol specifies a cardioprotective pacing sequence that includes alternating pacing and non-pacing periods or alternating pacing modes for delivering pacing during a revascularization procedure such as a PTCA procedure.

In one embodiment, pacing protocol module 227 is configured to be detachably connected to external pacemaker 222. In a specific embodiment, pacing protocol module 227 includes a memory device that stores the cardioprotective pacing protocol, and control circuit 226 is capable of automatically executing the cardioprotective pacing protocol when pacing protocol module 227 is connected to external pacemaker 222. In another specific embodiment, in addition to the memory device that stores the cardioprotective pacing protocol, pacing protocol module 227 includes a user interface that allows the user to adjust parameters of the cardioprotective pacing protocol and/or control circuitry that supplement the functions of control circuit 226 for automatically executing the cardioprotective pacing protocol. In various embodiments, other pacing protocol modules are provided for automatically executing pacing protocols using external pacemaker 222. In various embodiments, the user is provided with external pacemaker 222 and pacing protocol modules for executing pacing protocols such as the cardioprotective pacing protocol, cardiac resynchronization therapy (CRT) pacing protocol, and cardiac remodeling control therapy (RCT) pacing protocol. Compared to a PSA that requires the user to manually adjust pacing parameters during a test or therapy session, the automatic execution of the pacing protocol increases the accuracy of pacing control and reduces or eliminates the need for the user to control the delivery of the pacing pulses, so that the user can be more attentive to the response of the patient and/or the revascularization procedure.

In various embodiments, external pacemaker 222, including its various elements in various embodiments, is implemented using a combination of hardware and software. In various embodiments, each element of external pacemaker 222 may be implemented using an application-specific circuit constructed to perform one or more specific functions or a general-purpose circuit programmed to perform such function(s). Such a general-purpose circuit includes, but is not limited to, a microprocessor or a portion thereof, or other programmable logic circuit or a portion thereof. In one embodiment, control circuit 226 is implemented as a microprocessor-based circuit programmed to perform various functions discussed in this document.

Cardioprotective Pacing Protocol

Figure 3:
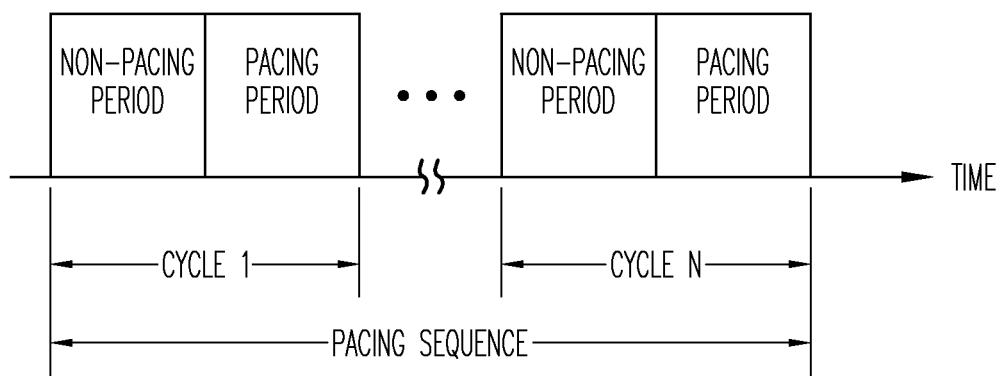
FIG. 3 is a timing diagram illustrating an embodiment of a cardioprotective pacing protocol.

FIG. 3 is a timing diagram illustrating an embodiment of a cardioprotective pacing protocol that specifies a pacing sequence. In one embodiment, the cardioprotective pacing protocol is a PPC protocol for delivering the cardioprotective pacing sequence after the insertion of a PTVI device into body 102 during a revascularization procedure. In various embodiments, the pacing sequence is applied before, during, and/or after the occlusion of the blood vessel during the revascularization procedure to provide cardioprotection against anticipated ischemic and/or reperfusion injuries.

The pacing sequence includes alternating non-pacing and pacing periods. As illustrated in FIG. 3, the pacing sequence includes a specified number (N) of cycles each including a non-pacing period followed by a pacing period. In various embodiments, delivery of pacing pulses is controlled according to a non-pacing mode during each of the non-pacing periods and according to a stress augmentation pacing mode during each of the pacing periods. Under the non-pacing mode, no pacing pulse is timed to be delivered. Under the stress augmentation pacing mode, pacing pulses are delivered to augment mechanical stress on the myocardium of the heart to a level effecting cardioprotection against myocardial injury. When a pacing pulse is timed to be delivered, it will be delivered unless inhibited by an inhibitory event such as a detected intrinsic cardiac depolarization occurring before the scheduled delivery of the pacing pulse during a cardiac cycle. Under the non-pacing mode according to which no pacing pulse is timed to be delivered, the non-delivery is due to programming rather than inhibition by a detected inhibitory event. In various embodiments, the stress augmentation pacing mode is a standard or non-standard pacing mode with pacing parameter values selected for the desired level of myocardial stress augmentation according to the patients' needs, conditions, and responses. Examples of the stress augmentation pacing mode includes an atrial tracking pacing mode (such as VDD and DDD modes) with a relatively short atrioventricular AV delay, a bradycardia pacing mode with a pacing rate substantially higher than the patient's intrinsic heart rate, and an asynchronous pacing mode with a pacing rate substantially higher than the patient's intrinsic heart rate.

In various embodiments, the cardioprotective pacing protocol specifies pacing parameters including, but not limited to, the number of cycles (N), the pacing period, the non-pacing period, and the pacing rate (such as the lower rate limit and the upper rate limit). In one embodiment, the pacing parameters are empirically derived. In one embodiment, because the efficacy and safety of the therapy also depend on the number of pacing pulses that actually result in paced cardiac contractions and presence of arrhythmic conditions, among other things, the pacing parameters are adjusted for each patient according to the patient's conditions at the time of the therapy. The delivery of the therapy is monitored, and the pacing parameters are dynamically adjusted to ensure effectiveness in cardioprotection. In various embodiments, the cardioprotective pacing protocol specifies response to safety events that indicate a need to stop or adjust the delivery of the pacing sequence for the safety of the patient. Examples of such safety events include various types of arrhythmia such as atrial fibrillation (AF), ventricular tachycardia (VT) and ventricular fibrillation (VT). In one embodiment, the cardioprotective pacing protocol specifies an upper rate limit being a maximum pacing rate. In one embodiment, the cardioprotective pacing protocol specifies a default upper rate limit that can be overridden by the user, but also specifies a maximum value up to which the upper rate limit is programmable by the user.

PTVI Device with Pacing Electrode(s)

Figure 4:
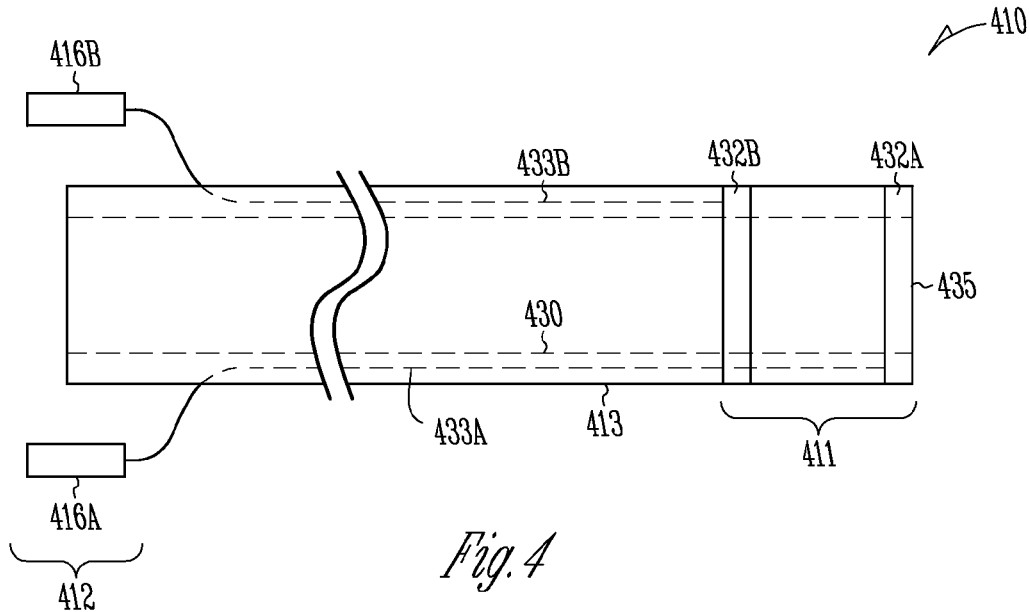
FIG. 4 is an illustration of an embodiment of a guide catheter with pacing electrodes.
Figure 5:
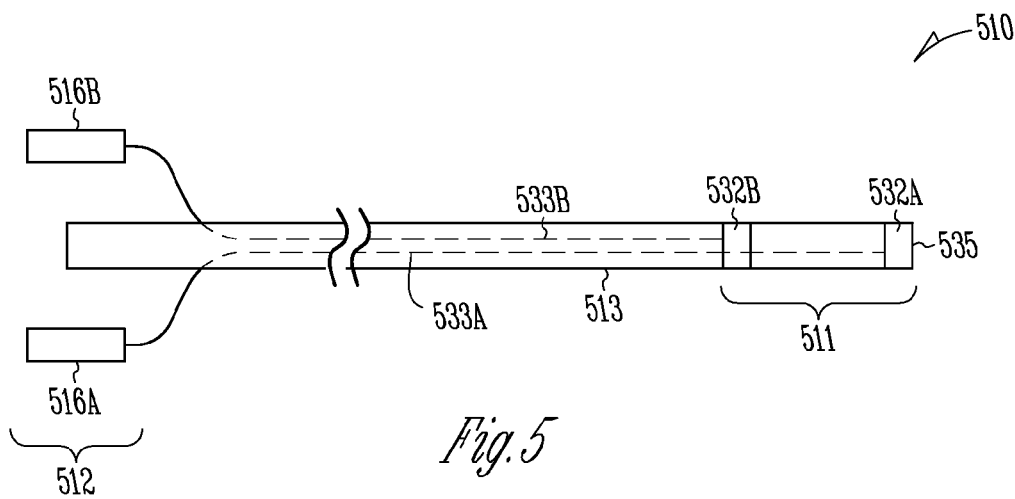
FIG. 5 is an illustration of an embodiment of a guide wire with pacing electrodes.
Figure 6:
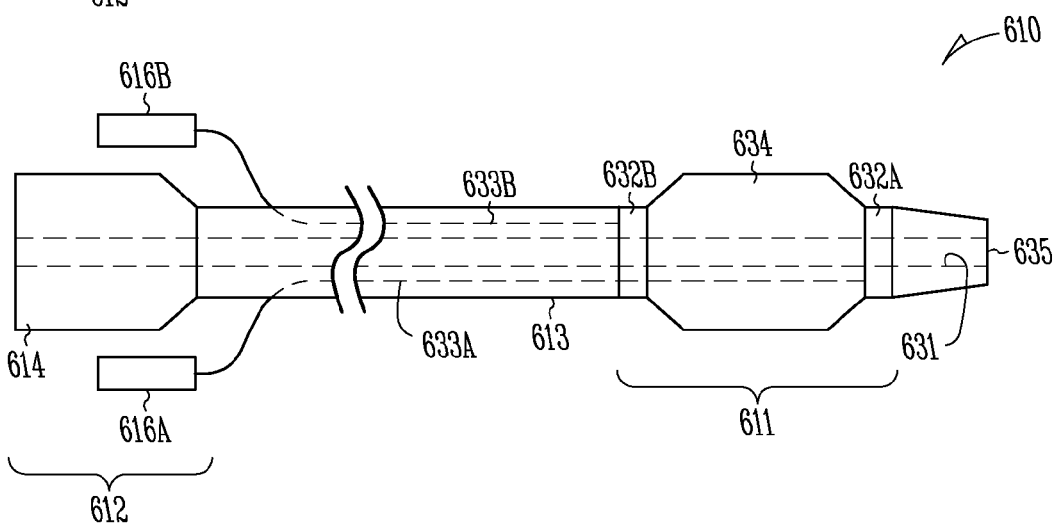
FIG. 6 is an illustration of an embodiment of an angioplasty catheter with pacing electrodes.

FIGS. 4-6 illustrate a PTVI device assembly that includes a guide catheter, a guide wire, and an angioplasty catheter. During a revascularization procedure such as a PTCA procedure, the guide catheter is inserted into the patient first, followed by the guide wire through a lumen of the guide catheter. The angioplasty catheter includes a lumen that accommodates a portion of the guide wire, thereby allowing the angioplasty catheter to be inserted into the patient through the guide catheter and over the guide wire. The guide catheter, guide wire, and angioplasty catheter are inserted in such a way that allows an angioplasty device, such as a balloon, of the angioplasty catheter to be placed in the portion of a blocked blood vessel that is to be reopened during the revascularization procedure.

FIG. 4 is an illustration of an embodiment of a guide catheter 410. Guide catheter 410 is an embodiment of PTVI device 110 and has an elongate shaft 413 between a distal end portion 411 and a proximal end portion 412. Distal end portion 411 is configured for intravascular placement and includes a distal tip 435. A lumen 430 extends within shaft 413 and has a proximal opening in proximal end portion 412 and a distal opening at distal tip 435. Lumen 430 accommodates at least a portion of the angioplasty catheter. Distal end portion 411 includes pacing electrodes 432A-B. In the illustrated embodiment, electrode 432A is incorporated onto distal tip 435. Conductor 433A is connected between pacing electrode 432A and a connector 416A. Conductor 433B is connected between pacing electrode 432B and a connector 416B. Connectors 416A-B are each part of proximal end portion 412. In one embodiment, conductors 433A-B each extend longitudinally within shaft 413. In another embodiment, conductors 433A-B each extend longitudinally on the outer surface of shaft 413 and are insulated.

In one embodiment, guide catheter 410 has a length in a range of approximately 50 cm to 150 cm. Shaft 413 has an outer diameter in a range of approximately 0.5 mm to 8 mm, and lumen 430 has a diameter in a range of approximately 0.4 mm to 7 mm. Conductors 433A-B are made of a metallic material such as stainless steel or an alloy of nickel, titanium, cobalt, gold, and/or silver chloride. Elongate shaft 413 is made of a material such as silicone, polyurethane, Teflon, or polytetrafluoroethylene (PTFE). Electrodes 432A-B are made of a metallic material such as platinum or an iridium alloy.

FIG. 5 is an illustration of an embodiment of a guide wire 510. Guide wire 510 is an embodiment of PTVI device 110 and has an elongate shaft 513 between a distal end portion 511 and a proximal end portion 512. Distal end portion 511 is configured for intravascular placement and includes a distal tip 535. Distal end portion 511 includes pacing electrodes 532A-B. In the illustrated embodiment, electrode 532A is incorporated onto distal tip 535. Conductor 533A is connected between pacing electrode 532A and a connector 516A. Conductor 533B is connected between pacing electrode 532B and a connector 516B. Connectors 516A-B are each part of proximal end portion 512. In one embodiment, conductors 533A-B each extend longitudinally within shaft 513. In another embodiment, conductors 533A-B each extend longitudinally on the outer surface of shaft 513 and are insulated. In one embodiment, one of connectors 533A-B is the core of guide wire 510.

In one embodiment, guide wire 510 has a length in a range of approximately 30 cm to 300 cm. Shaft 513 is an elongate cylindrical shaft having a diameter in a range of approximately 0.2 mm to 1.5 mm. Conductors 533A-B are made of a metallic material such as stainless steel or an alloy of nickel, titanium, and/or cobalt. Elongate shaft 513 is made of a material such as silicone, polyurethane, Teflon, or polytetrafluoroethylene (PTFE). Electrodes 532A-B are made of a metallic material such as platinum, an iridium alloy, gold, or silver chloride.

FIG. 6 is an illustration of an embodiment of an angioplasty catheter 610. Angioplasty catheter 610 is an embodiment of PTVI device 110 and has an elongate shaft 613 between a distal end portion 611 and a proximal end portion 612. A lumen 631 longitudinally extends within shaft 613 to accommodate at least a portion of a guide wire such as guide wire 510. Distal end portion 611 is configured for intravascular placement and includes a distal tip 635 and an angioplasty device 634. Angioplasty device 634 has one end approximately adjacent to distal tip 635 and another end coupled to shaft 613. In one embodiment, angioplasty device 634 includes an adjustable portion that has controllable expandability and contractibility. In the illustrated embodiment, angioplasty device 634 includes a balloon that is inflated and deflated through a lumen 631 longitudinally extending within shaft 613 and connected between the chamber of the balloon and a connector 614 at proximal end portion 612. The balloon is inflatable using an air or liquid pump connected to that connector. In various embodiments, angioplasty device 634 includes a balloon or other device that allows for application of an angioplasty therapy such as vascular dilatation, stent delivery, brachytherapy (radiotherapy), atherectomy, or embolic protection. In one embodiment, distal tip 635 is a tapered tip that facilitates the insertion of angioplasty catheter 610 into a blood vessel. Distal end portion 611 includes pacing electrodes 632A-B. In the illustrated embodiment, pacing electrode 632A is approximately adjacent to one end of angioplasty device 634, and pacing electrode 632B is approximately adjacent to the other end of angioplasty device 634. A conductor 633A extends longitudinally within shaft 613 and is connected between pacing electrode 632A and a pacing connector 616A, which is part of proximal end portion 612. A conductor 633B extends longitudinally within elongate shaft 613 and is connected between pacing electrode 632B and a pacing connector 616B, which is also part of proximal end portion 612. In an alternative embodiment, pacing connectors 616A-B are physically integrated into one multi-conductor connector. Proximal end portion 612 also includes a proximal end device 614. In various embodiments, connector 614 includes a structure that accommodates all the mechanical connection and access requirements for angioplasty catheter 610, which depend on the function of angioplasty device 634. In one embodiment, connector 614 includes an integrated device. In another embodiment, connector 614 branches out into multiple connectors and/or other devices.

In one embodiment, angioplasty catheter 610 has a length in a range of approximately 50 cm to 150 cm. Shaft 613 is an elongate cylindrical shaft having a diameter in a range of approximately 1 mm to 5 mm. In one embodiment, angioplasty device 634 has an adjustable, substantially cylindrical or semi-spherical shape with a maximum diameter in a range of approximately 1 mm to 10 mm when fully expanded and a maximum diameter in a range of approximately 0.5 mm to 5 mm when fully contracted. In one embodiment, conductors 633A-B are each made of a metallic material such as stainless steel or an alloy of nickel, titanium, and/or cobalt. Electrodes 632A-B are each made of a metallic material such as platinum or an iridium alloy. Elongate shaft 613 has a tubular outer shell made of a material such as silicone, polyurethane, Teflon, or polytetrafluoroethylene (PTFE).

Guide catheter 410, guide wire 510, and angioplasty device 610 are illustrated in FIGS. 4-6 for illustrative but not restrictive purposes. For example, one or more pacing electrodes can be distributed on each of these PTVI devices in any way allowing delivery of pacing pulses to desirable locations. In various embodiments, one or more pacing electrodes are incorporated onto one or more of guide catheter 410, guide wire 510, and angioplasty device 610 for delivering pacing pulses through the PTVI device assembly including these three devices. In one embodiment, one or more defibrillation electrodes are also incorporated onto one or more of guide catheter 410, guide wire 510, and angioplasty device 610 for delivering defibrillation shocks through the PTVI device assembly. In one embodiment, one or more pacing electrodes such as one of more of pacing electrodes 432A-B, 532A-B, and 632A-B are made of conductive radiopaque material to function as one or more radiopaque markers for locating guide catheter 410, guide wire 510, and/or angioplasty device 610 using fluoroscopy.

In one embodiment, angioplasty device 610 includes a balloon. Guide wire 510 remains within lumen 631 when the balloon is inflated. The inflated balloon is over pacing electrodes 532A-B. When being deflated, the balloon is retracted to expose electrodes 532A-B, thereby allowing delivery of pacing pulses. In one embodiment, shaft 613 includes a portion having an adjustable length that is shortened to expose electrodes 532A-B when the balloon is deflated.

In one application during a PTCA procedure for reopening, for example, right coronary artery 107, guide catheter 410 is inserted into femoral artery 104 and advanced to aorta 106 until distal tip 435 reaches the point where right coronary artery 107 branches from aorta 106. Guide wire 510 is introduced through lumen 430 of guide catheter 410 until distal end 535 is in right coronary artery 107. Angioplasty catheter 610 is then introduced through lumen 430 over guide wire 510 until angioplasty device 634 (balloon) is in the portion of right coronary artery 107. In one embodiment, the acute pacing cardioprotection therapy is delivered using electrodes 432A-B as soon as guide catheter 410 is in place for the PTCA procedure. In one embodiment, when the PTVI device assembly including guide catheter 410, guide wire 510, and angioplasty device 610 are in place for the PTCA procedure, the acute pacing cardioprotection therapy is delivered using one or more pairs of pacing electrodes selected from electrodes 432A-B, 532A-B, 632A-B, and 119.

In one embodiment, the PTVI device assembly allows for combined pacing cardioprotection therapy and ischemic cardioprotection therapy. For example, the ischemic cardioprotection therapy is applied by intermittently occluding a blocked vessel by inflating and deflating angioplasty device 634 (balloon) of angioplasty catheter 610, in addition to delivering the pacing cardioprotection therapy through the one or more pairs of pacing electrodes.

Various embodiments of the PTVI devices and the pacemaker are discussed below as examples illustrating the pacing system for delivering the acute pacing cardioprotection therapy during a revascularization procedure. In general, such a pacing system includes a pacemaker capable of delivering pacing pulses according to a cardioprotective pacing protocol, such as discussed above with reference to FIG. 3, and one or more PTVI devices each including one or more pacing electrodes. In one embodiment, the one or more PTVI devices includes devices used to perform the revascularization procedure, such as guide catheters, guide wires, and angioplasty catheters, that are modified to allow delivery of the acute pacing cardioprotection therapy. In another embodiment, the one or more PTVI devices includes one or more devices that are not required to perform the revascularization procedure itself but configured to allow delivery of pacing pulses during the revascularization procedure. For example, if the stress augmentation pacing mode is an atrial tracking pacing mode (such as VDD mode or DDD mode), a lead in addition to the PTVI device may be required for placing one or more electrodes in an atrium, or the PTVI device may be configured to include one or more electrodes in or adjacent an atrium and one or more electrodes in a blood vessel over a ventricle. In various embodiments, the PTVI devices have sizes identical or similar to those discussed above, and are constructed using materials identical or similar to those discussed above.

EXAMPLE

External Pacemaker with Pacing Protocol Module

Figure 7:
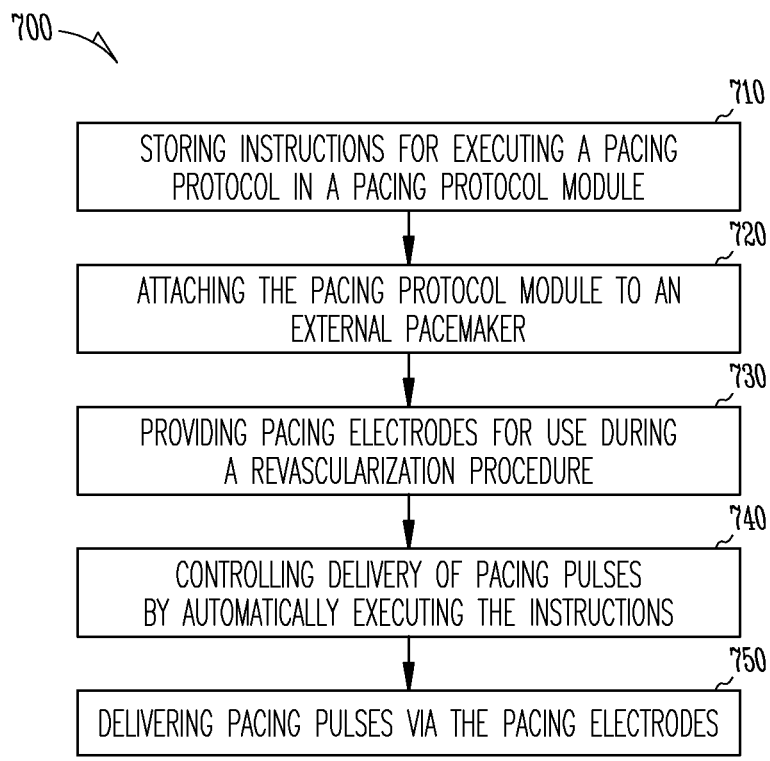
FIG. 7 is a flow chart illustrating an embodiment of a method for delivering pacing during revascularization.

FIG. 7 is a flow chart illustrating of an embodiment of a method 700 for delivering pacing during revascularization. Method 700 uses a pacing system executing an automatic pacing protocol specifying times and values for dynamic pacing parameter changes, eliminating the need for manual adjustment of pacing parameters. In various embodiments, the pacing system is connected to one or more of the PTVI devices discussed in this document to deliver pacing pulses through one or more pacing electrodes incorporated onto the one or more PTVI devices.

Instructions for executing a pacing protocol are stored in a pacing protocol module at 710. The pacing protocol specifies, among other things, a pacing algorithm and its parameters, including timing for changing the parameters. In one embodiment, the pacing protocol is a cardioprotective pacing protocol for delivering pacing during a revascularization procedure, such as the cardioprotective pacing protocol discussed above with reference to FIG. 3. In one embodiment, the cardioprotective pacing protocol is executed to deliver pacing pulses during a revascularization procedure such as a PTCA procedure. Such an acute pacing cardioprotection therapy, also referred to as a PPC therapy, is applied peri-PTCA procedure to limit the myocardial injury caused by MI and reperfusion, thereby limiting the size of infarcted myocardial tissue in the heart of the patient in whom the revascularization procedure is performed. In one embodiment, the instructions stored in the pacing protocol module include one or more PPC protocols and instructions for generating a current pacing protocol for each PPC therapy using the one or more PPC protocols and one or more parameters measured from the patient, such as the PPC therapy is tailored to the patient to ensure safety and efficacy. In this document, a "current pacing protocol" refers to the pacing protocol that is made ready for execution during a therapy.

The pacing protocol module is attached to an external pacemaker at 720. In one embodiment, the pacing protocol module includes a storage medium and an interface for connecting to an external pacemaker such as a PSA. With the pacing protocol module connected, the external pacemaker is capable of automatically executing the current pacing protocol. An example of a pacing system including the pacing protocol module and the external pacemaker is discussed below, with reference to FIGS. 8-15.

Pacing electrodes are provided for use during the revascularization procedure at 730. The pacing electrodes includes one or more pacing electrodes incorporated onto one or more PTVI devices as discussed above. In one embodiment, the pacing electrodes also include additional one or more pacing electrodes not incorporated onto a PTVI device, such as implantable electrodes in the patient and surface electrodes for attachment onto the patient's skin.

The delivering of the pacing pulses are controlled by automatically executing the instructions at 740, using the pacing system including the pacing protocol module and the external pacemaker. The pacing pulses are delivered via the pacing electrodes at 750.

Figure 8:
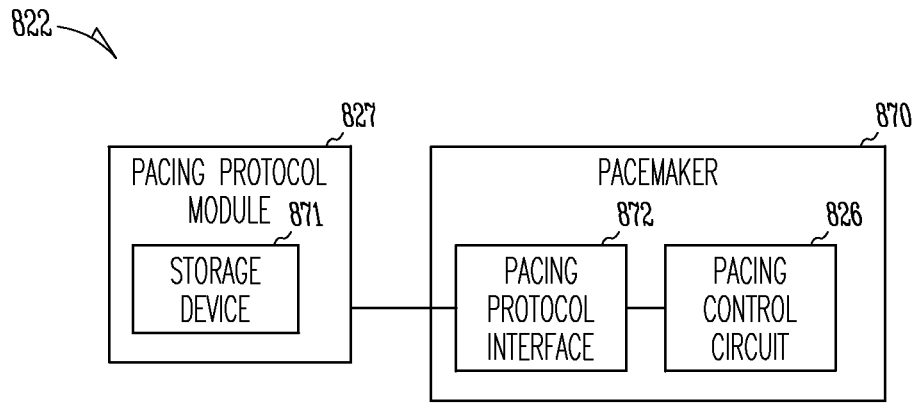
FIG. 8 is a block diagram illustrating an embodiment of an external pacemaker.

FIG. 8 is a block diagram illustrating of an embodiment of an external pacemaker 822, which is another embodiment of external pacemaker 222. External pacemaker 822 includes a pacemaker 870 and a pacing protocol module 827. Pacemaker 870 includes a pacing protocol interface 872 and a pacing control circuit 826. Pacing protocol interface 872 receives machine-readable instructions for automatically executing a current pacing protocol.

Pacing control circuit 826 controls delivery of pacing pulses by automatically executing the current pacing protocol according to the received machine-readable instructions. In one embodiment, as further discussed with reference to FIGS. 12 and 13, pacing control circuit 826 is housed in a pacemaker chassis. Pacing protocol module 827 is external to the pacemaker chassis and is configured to be attached to pacemaker 870 and electrically connected to pacing protocol interface 872. Pacing protocol module 827 includes a storage device 871 that contains the machine-readable instructions for automatically executing the current pacing protocol. In one embodiment, as further discussed with reference to FIGS. 12 and 13, storage device 871 is housed in a protocol chassis. In various embodiments, the machine-readable instructions include instructions for automatically generating the current pacing protocol using one or more pacing protocols stored in storage device 871.

In one embodiment, the current pacing protocol provides for control of delivery of a pacing therapy through one or more PTVI devices such as those discussed in this document. The current pacing protocol is a cardioprotective pacing protocol such as discussed above with reference to FIG. 3. The cardioprotective pacing protocol provides for control of a PPC therapy during a revascularization procedure. In one embodiment, the current pacing protocol is a patient-specific pacing protocol generated for an individual patient using one or more parameters indicative of the patient's cardiac conditions. A pacing system allowing for generation of such a patient-specific pacing protocol is further discussed with reference to FIGS. 14-17.

Figure 9:
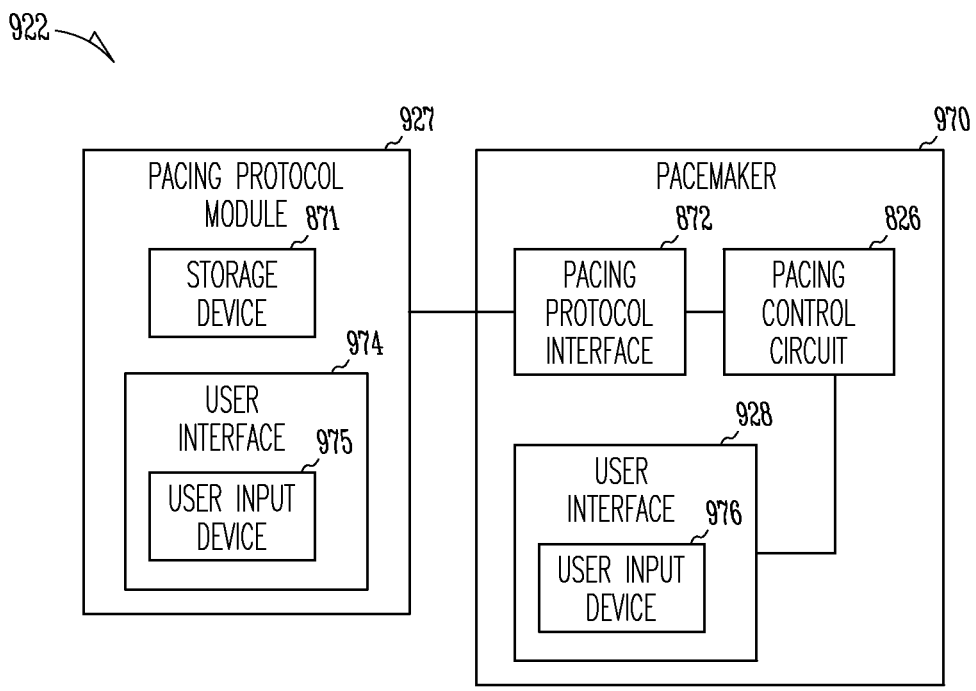
FIG. 9 is a block diagram illustrating another embodiment of an external pacemaker.

FIG. 9 is a block diagram illustrating of an embodiment of an external pacemaker 922, which is another embodiment of external pacemaker 822. External pacemaker 922 includes a pacemaker 970 and a pacing protocol module 927. Pacemaker 970 is another embodiment of pacemaker 870 and includes pacing protocol interface 872, pacing control circuit 826, and a pacemaker user interface 928. User interface 928 includes a user input device 976 that allows a user such as a physician or other caregiver to adjust user-adjustable pacing parameters of the current pacing protocol. Pacing protocol module 927 is another embodiment of pacing protocol module 827. In the illustrated embodiment, pacing protocol module 927 includes storage device 871 and protocol user interface 974. User interface 974 includes a user input device 975 that allows the user to adjust user-adjustable pacing parameters of the current pacing protocol. In another embodiment, pacing protocol module 927 does not include a user interface, and all the user-adjustable pacing parameters are adjusted using user interface 928 of pacemaker 970. In various embodiments, external pacemaker 922 includes one or both of user interfaces 974 and 928.

In one embodiment, pacemaker 970 includes a pacemaker chassis that houses at least pacing control circuit 826. In one embodiment, portions of pacing protocol interface 872 and user interface 928, including user input device 976, are mounted on the pacemaker chassis. In one embodiment, pacing protocol module 927 includes a protocol chassis that houses at least storage device 871. In one embodiment, portions of user interface 974, including user input device 975, are mounted on the protocol chassis.

Figure 10:
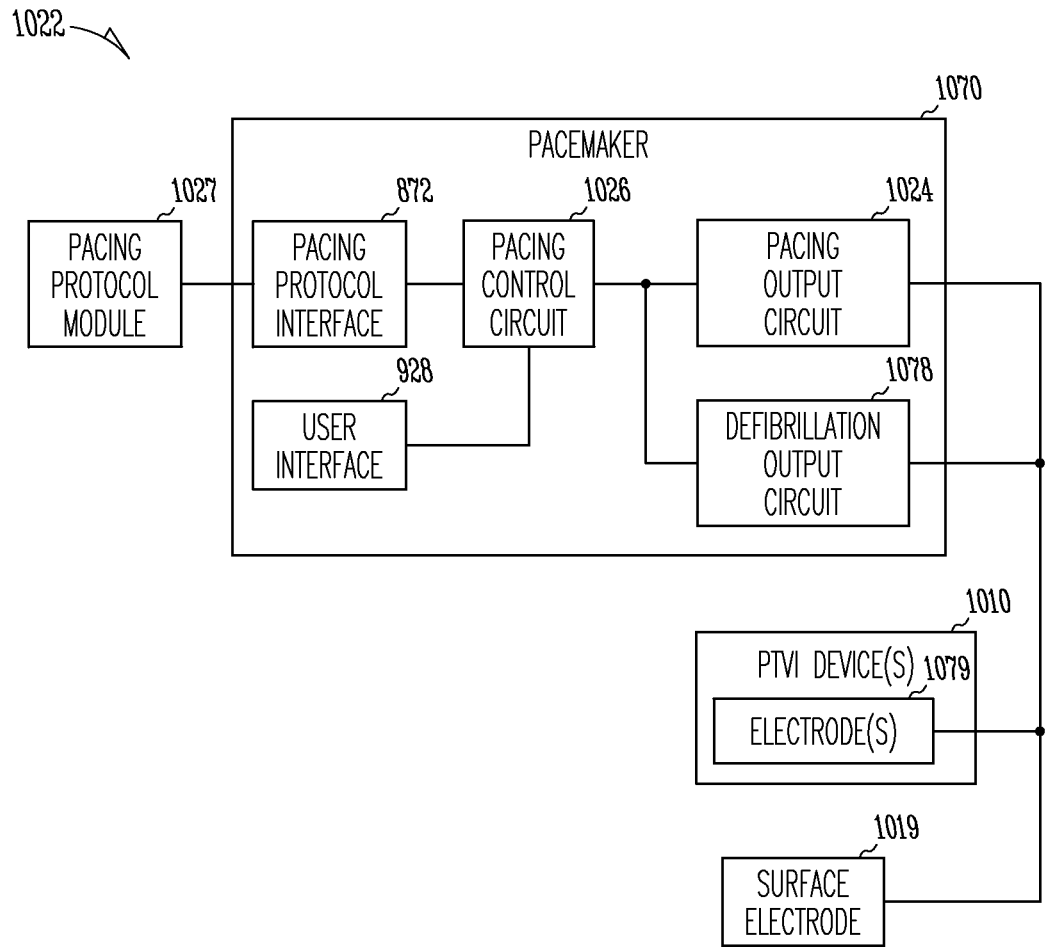
FIG. 10 is a block diagram illustrating an embodiment of an external pacemaker and electrodes.

FIG. 10 is a block diagram illustrating of an embodiment of a pacing system including an external pacemaker 1022 connected to electrodes. External pacemaker 1022 is another embodiment of external pacemaker 822 and includes a pacemaker 1070 and a pacing protocol module 1027. Pacemaker 1070 is another embodiment of pacemaker 870 and includes pacing protocol interface 872, a pacing control circuit 1026, user interface 928, a pacing output circuit 1024, and a defibrillation output circuit 1078. Pacing control circuit 1026 controls delivery of cardioversion/defibrillation shocks in addition to performing the functions of pacing control circuit 826. Pacing output circuit 1024 delivers pacing pulses through at least one of electrode(s) 1079 of PTVI device(s) 1010. Examples of electrode(s) 1079 include the electrodes incorporated onto the PTVI devices discussed in this document. Defibrillation output circuit 1078 delivers cardioversion/defibrillation shocks through at least one of electrode(s) 1079. In one embodiment, a surface electrode 1019 attached to the skin of the patient is also used for delivering the pacing pulses and/or cardioversion/defibrillation shocks. Pacing protocol module 1027 includes pacing protocol module 827 or 927.

In one embodiment, pacemaker 1070 is a PSA including a pacemaker chassis that houses at least pacing control circuit 1026, pacing output circuit 1024, and defibrillation output circuit 1078. In one embodiment, portions of pacing protocol interface 872 and user interface 928, including user input device 976, are mounted on the pacemaker chassis.

Figure 11:
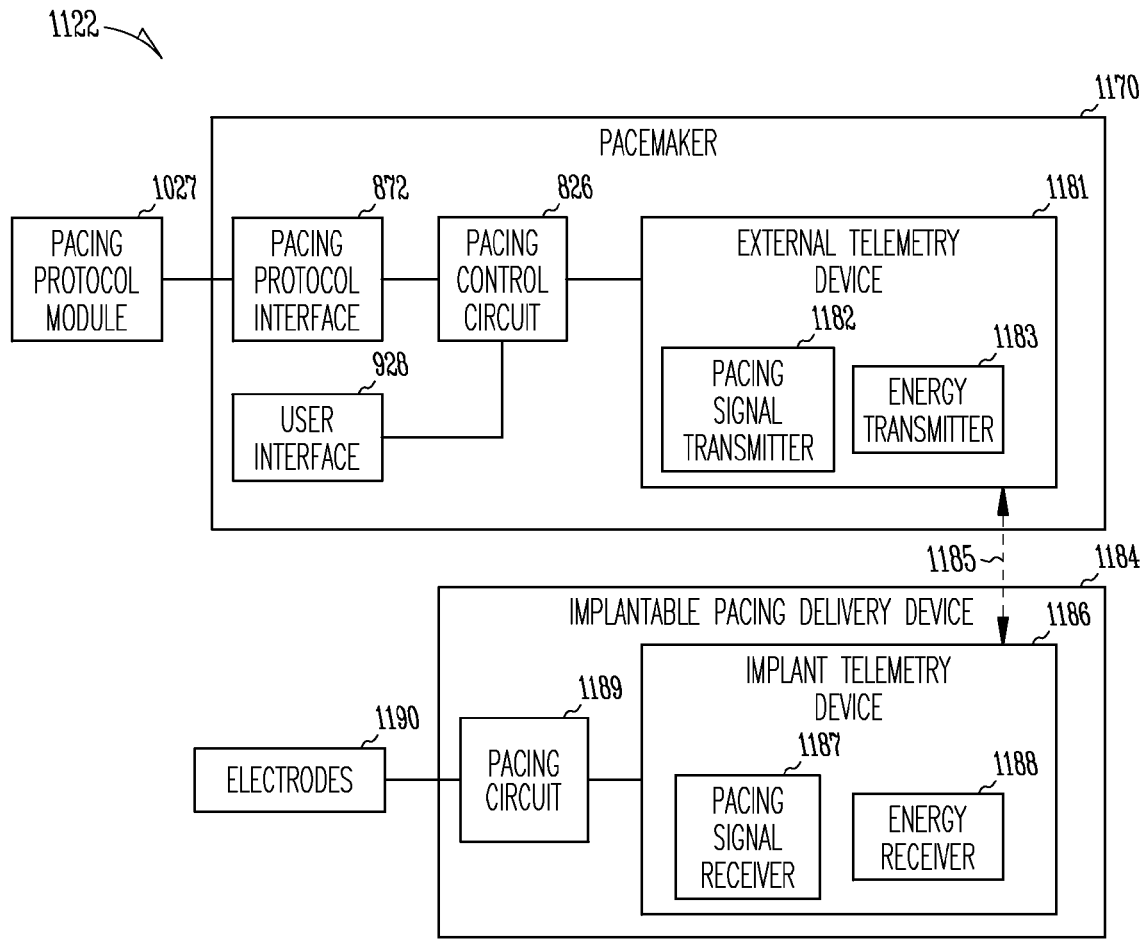
FIG. 11 is a block diagram illustrating an embodiment of an external pacemaker and an implantable pacing delivery device.

FIG. 11 is a block diagram illustrating of an embodiment of a pacing system including an external pacemaker 1122 and an implantable pacing delivery device connected to electrodes 1190. External pacemaker 1122 is another embodiment of external pacemaker 822 and includes a pacemaker 1170 and pacing protocol module 1027. Pacemaker 1170 is another embodiment of pacemaker 870 and includes pacing protocol interface 872, pacing control circuit 826, user interface 928, and an external telemetry device 1181. Implantable pacing delivery device 1184 includes a pacing output circuit 1189 and an implant telemetry device 1186. Pacing output circuit 1189 delivers the pacing pulses through electrodes 1190 in response to pacing signals generated by pacing control circuit 826 and transmitted via a telemetry link 1185 supported by external telemetry device 1181 and implant telemetry device 1186. Electrodes 1190 includes pacing electrodes incorporated onto implantable pacing delivery device 1184 or electrically connected to implantable pacing delivery device 1184 through one or more implantable pacing leads.

In the illustrated embodiment, telemetry link 1185 is an inductive couple capable of transcutaneous signal and energy transmission. External telemetry device 1181 includes a pacing signal transmitter 1182 and an energy transmitter 1183. Pacing signal transmitter 1182 transmits the pacing signals for controlling the delivery of the pacing pulses. Energy transmitter 1183 transmits the energy required for implantable pacing delivery device 1184 to deliver the pacing pulses. Implant telemetry device 1186 includes a pacing signal receiver 1187 and an energy receiver 1188. Pacing signal receiver 1187 receives the pacing signals transmitted from pacing signal transmitter 1182. Energy receiver 1188 receives the energy transmitted from energy transmitter 1183.

In one embodiment, pacemaker 1170 includes a pacemaker chassis that houses at least pacing control circuit 826 and external telemetry device 1181. In one embodiment, portions of pacing protocol interface 872 and user interface 928, including user input device 976, are mounted on the pacemaker chassis.

Figure 12:
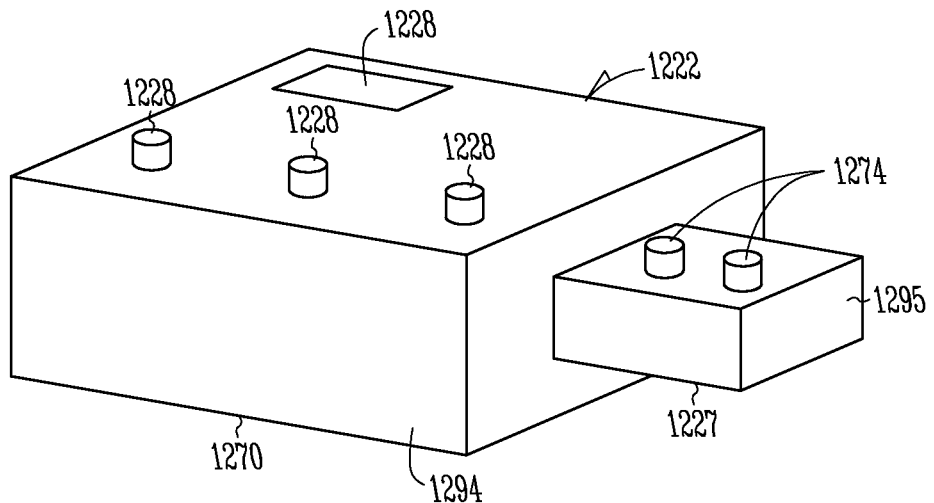
FIG. 12 is an illustration of an embodiment of the external pacemaker of FIGS. 8-11.

FIG. 12 is an illustration of an embodiment of the exterior configuration of an external pacemaker 1222 including a pacemaker 1270 and a pacing protocol module 1227. Examples of pacemaker 1270 include pacemakers 870, 970, 1070, and 1170 as discussed above. An example of pacing protocol module 1227 includes pacing protocol module 927.

In the illustrated embodiment, pacemaker 1270 includes a pacemaker chassis 1294 housing its circuitry and portions of a pacemaker user interface 1228 mounted on pacemaker chassis 1294. Pacing protocol module 1227 includes a protocol chassis 1295 housing its circuitry and portions of a protocol user interface 1274 mounted on protocol chassis 1295. Pacing protocol module 1227 is attached to pacemaker 1270. In one embodiment, pacing protocol module 1227 is detachably attached to pacemaker 1270. This allows pacemaker 1270 to execute various type pacing protocols by providing pacing protocol modules 1227 each storing one or more pacing protocols of one type.

Figure 13:
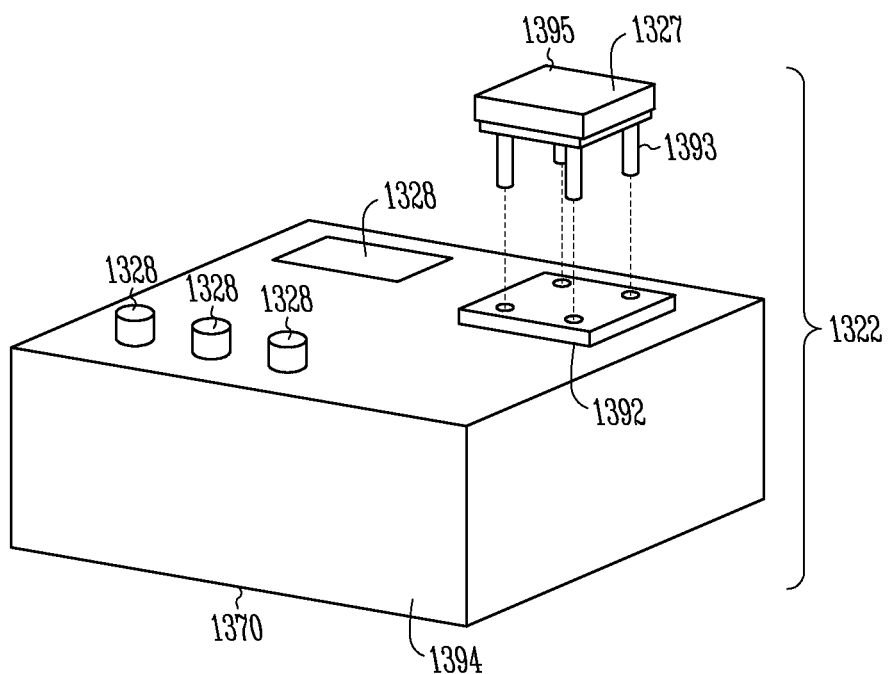
FIG. 13 is an illustration of another embodiment of the external pacemaker of FIGS. 8-11.

FIG. 13 is an illustration of an embodiment of the exterior configuration of an external pacemaker 1322 including a pacemaker 1370 and a pacing protocol module 1327. Examples of pacemaker 1370 include pacemakers 870, 970, 1070, and 1170 as discussed above. An example of pacing protocol module 1327 includes pacing protocol module 827.

In the illustrated embodiment, pacemaker 1370 includes a pacemaker chassis 1394 housing its circuitry and portions of a pacemaker user interface 1328 and a pacemaker connector 1392 mounted on pacemaker chassis 1394. Pacing protocol module 1327 includes a protocol chassis 1395 housing its circuitry and a protocol connector 1393 mounted on protocol chassis 1395. Pacing protocol module 1327 is configured as a plug-in module to be detachably attached to pacemaker 1370 by mating protocol connector 1393 with pacemaker connector 1394.

FIGS. 12 and 13 show examples of the external pacemaker for illustrative purposes. In various embodiments, the pacemaker and the pacing protocol module as discussed in this document have various exterior configurations. In embodiments illustrated in FIGS. 12 and 13, the pacing protocol module is externally attached to the pacemaker. In other embodiments, the pacing protocol module is also housed in the pacemaker chassis. In various embodiments, the pacing protocol module is configured in the forms of a plug-in module, a printed circuit board, a memory card, or an integrated circuit chip, that is detachably or non-detachably connected to the pacemaker to allow the pacemaker to generate and execute the current pacing protocols automatically.

Examples of Experimentally Determined Pacing Parameters

Pacing parameters specified in a PPC protocol, as discussed above with reference to FIG. 3, were evaluated in pre-clinical experiments by measuring effect of the PPC therapy in reducing infarct size (surface area of infracted tissue). The non-pacing period, the pacing period, and the number of cycles were programmed to various combination of values, and the reduction of the infarct size is evaluated for each combination of values.

The following are examples of combinations of parameter values that resulted in substantial reduction of the infarct size in pre-clinical experiments:
  the non-pacing period is 30 seconds, the pacing period is 30 seconds, and the number of cycles is 10.
  the non-pacing period is 20 seconds, the pacing period is 20 seconds, and the number of cycles is 10.
  the non-pacing period is 10 seconds, the pacing period is 10 seconds, and the number of cycles is 10.
  the non-pacing period is 15 seconds, the pacing period is 5 seconds, and the number of cycles is 10.

The following are examples of combination of parameter values that did not result in substantial reduction of the infarct size in the pre-clinical experiments:

- the non-pacing period is 30 seconds, the pacing period is 30 seconds, and the number of cycles is 5.
- the non-pacing period is 20 seconds, the pacing period is 20 seconds, and the number of cycles is 5.
- the non-pacing period is 10 seconds, the pacing period is 10 seconds, and the number of cycles is 5.
- the non-pacing period is 5 seconds, the pacing period is 5 seconds, and the number of cycles is 10.

In various embodiments, such experimentally derived values for the pacing parameters are used in one or more PPC protocols. In various embodiments, such experimentally derived values for the pacing parameters are used as default pacing parameters specified in the one or more PPC protocols. The generation of the current pacing protocol includes adjusting these pacing parameters based on the patient's specific conditions.

Pacing System for Automated Protocol Generation and Execution

Figure 14:
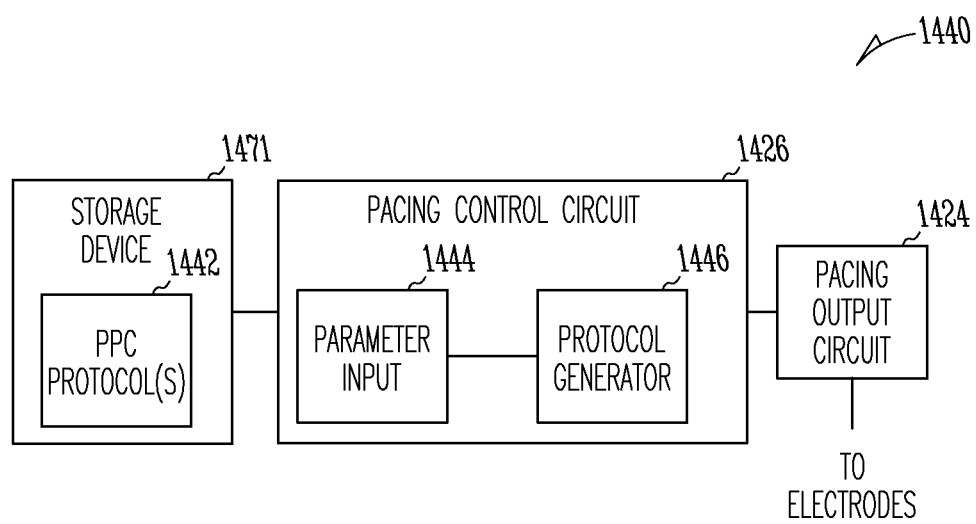
FIG. 14 is a block diagram illustrating an embodiment of a pacing system providing for pacing post-conditioning (PPC) therapy during revascularization.

FIG. 14 is a block diagram illustrating an embodiment of a pacing system 1440 providing for PPC therapy during revascularization. System 1440 is an embodiment of system 140. In addition to the values of the pacing parameters that can be empirically determined, system 1440 ensures efficacy and safety of the PPC therapy by generating the current pacing protocol using factors such as the patient's physiological and pathological conditions and whether each pacing pulse actually captures the heart.

System 1440 includes a pacing output circuit 1424, a storage device 1471, and a pacing control circuit 1426. Pacing output circuit 1424 delivers pacing pulses. Storage device 1471 stores one or more PPC protocols 1442. PPC protocol(s) 1442 each specify a pacing sequence including alternating non-pacing and pacing periods, as discussed above with reference to FIG. 3. The non-pacing periods each include a non-pacing duration during which no pacing pulse is timed to be delivered. The pacing periods each include a pacing duration during which a plurality of pacing pulses is timed to be delivered according to a stress augmentation pacing mode adapted to augment myocardial mechanical stress to a level effecting cardioprotection against myocardial injury. Pacing control circuit 1426 is programmed to execute the current pacing protocol and includes a parameter input 1444 and a protocol generator 1446. Parameter input 1444 receives one or more protocol generation parameters including one or more physiological parameters. Protocol generator 1446 is programmed to generate the current pacing protocol using PPC protocol(s) 1442 and the one or more protocol generation parameters. The current pacing protocol specifies a plurality of pacing parameters for controlling delivery of the pacing pulses from pacing output circuit 1424. Protocol generator 1446 is programmed to calculate one or more pacing parameters of the plurality of pacing parameters using the one or more protocol generation parameters.

In one embodiment, PPC protocol(s) 1442 each include default parameters such as the experimentally derived pacing parameters as discussed above. In one embodiment, PPC protocol(s) 1442 include multiple PPC protocols each corresponding to one or more patient conditions that are detected from the patient.

Figure 15:
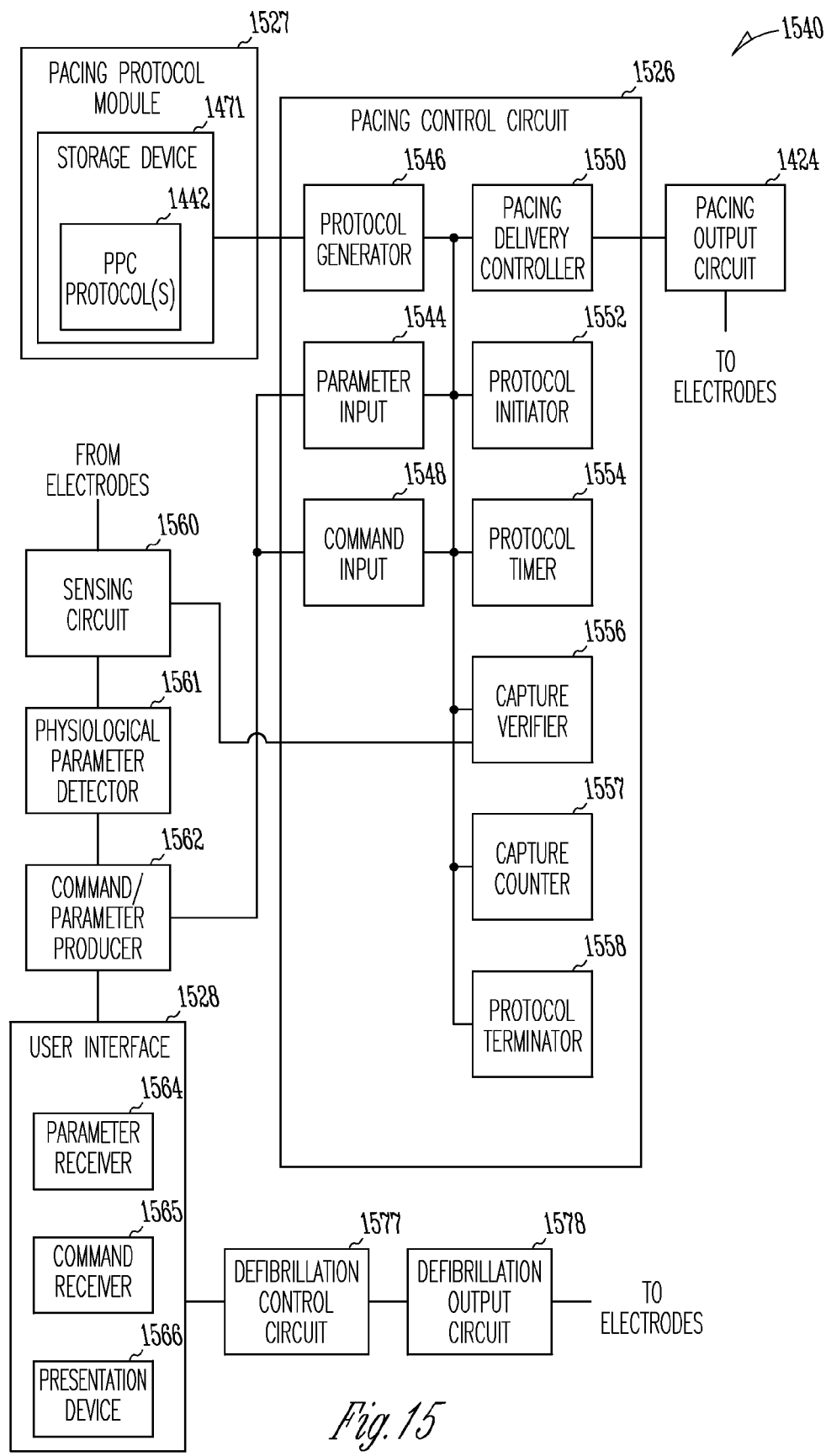
FIG. 15 is a block diagram illustrating another embodiment of the pacing system providing for PPC therapy during revascularization.

FIG. 15 is a block diagram illustrating an embodiment of a cardiac pacing system 1540, which is a specific embodiment of system 1440. System 1540 includes pacing output circuit 1424, a pacing control circuit 1526, a pacing protocol module 1527, a user interface 1528, a sensing circuit 1560, a physiological parameter detector 1561, and a command/parameter producer 1562. In one embodiment, as illustrated in FIG. 15, system 1540 also includes a defibrillation output circuit 1578 and a defibrillation control circuit 1577. In various embodiments, system 1540 is part of an external pacemaker such as one with functional elements illustrated as any of external pacemaker 822, 922, 1022, and 1122 and an exterior configuration illustrated as any of external pacemaker 1222 and 1322. Pacing protocol module 1527 is an embodiment of pacing protocol module 827, 927, or 1027 and is also illustrated as pacing protocol module 1227 or 1327.

Pacing output circuit 1424 delivers pacing pulses. Pacing control circuit 1526 is a specific embodiment of pacing control circuit 1426 and controls the delivery of the pacing pulses from pacing output circuit 1424 by executing a current pacing protocol that specifies a plurality of pacing parameters. For delivering a PPC therapy using the cardioprotective pacing protocol discussed with reference to FIG. 3, examples of the pacing parameters include the non-pacing period, the pacing period, the number of cycles each including a non-pacing period followed by a pacing period, and one or more pacing rates. In the illustrated embodiment, pacing control circuit 1526 includes a parameter input 1544, a command input 1548, a protocol generator 1546, a pacing delivery controller 1550, a protocol initiator 1552, a protocol timer 1554, a capture verifier 1556, a capture counter 1557, and a protocol terminator 1558.

Parameter input 1544 receives one or more protocol generation parameters that are used to generate the current pacing protocol. In various embodiments, the one or more protocol generation parameters include one or more pacing parameters specified in the current pacing protocol and/or one or more physiological parameters used to calculate one or more pacing parameters specified in the current pacing protocol. The one or more physiological parameters are measured from the patient receiving the PPC therapy. Examples of such physiological parameters include the heart rate and parameters indicative of arrhythmia or other conditions affecting the delivery and/or efficacy of the PPC therapy.

Command input 1548 receives one or more protocol execution commands. In various embodiments, the one or more protocol execution commands include one or more of a protocol initiation command for initiating an execution of the current pacing protocol and a protocol termination command for terminating the execution of the current pacing protocol.

Protocol generator 1546 generates the current pacing protocol using PPC protocol(s) 1442 and the one or more protocol generation parameters. PPC protocol(s) 1442 are stored in storage device 1471 of pacing protocol module 1527. In one embodiment, a plurality of PPC protocols 1442 is stored in storage device 1471. Protocol generator 1546 generates the current pacing protocol by selecting a protocol from the plurality of PPC protocols 1442 using the one and more protocol generation parameters. In another embodiment, protocol generator 1546 generates the current pacing protocol by receiving one PPC protocol 1442 from storage device 1471 and adjusting one or more pacing parameters specified in the received PPC protocol using the one and more protocol generation parameters. In one embodiment, protocol generator 1546 sets a pacing rate (such as a lower rate limit) to a value exceeding the patient's intrinsic heart rate by a specified margin for use in the current pacing protocol. In a specific embodiment, the margin is about 10-20 beats per minute. In another specific embodiment, the margin is a specified percentage of the heart rate.

Pacing delivery controller 1550 controls pacing output circuit 1424 for delivering the pacing pulses according to the current pacing protocol. Pacing delivery controller 1550 causes pacing output circuit 1424 to deliver the pacing pulses during the pacing period, and inhibits the delivery of the pacing pulses from pacing output circuit 1424 throughout the non-pacing period.

Protocol initiator 1552 initiates the execution of the current pacing protocol in response to the protocol initiation command. Protocol timer 1554 times the pacing sequence. In various embodiments, protocol timer 1554 times each of the non-pacing and pacing periods and counts the number of cycles each including a non-pacing period followed by a pacing period. In one embodiment, protocol timer 1554 also times the total pacing duration being the sum of the pacing periods and/or the total therapy duration being the sum of the pacing periods and non-pacing periods. Capture verifier 1556 verifies whether each of the delivered pacing pulses results in a captured beat (a cardiac depolarization resulting from a pacing pulse). Capture counter 1557 counts the number of the captured beats during the execution of the current pacing protocol.

Protocol terminator 1558 terminates the execution of the current pacing protocol. In one embodiment, protocol terminator 1558 terminates the execution of the current pacing protocol in response to the number of cycles reaching a specified number, the total pacing duration exceeding a specified minimum pacing time or the total therapy duration exceeding a specified minimum therapy time, and the number of the captured beats exceeding a specified minimum number of captured beats. These conditions for terminating the execution of the current pacing protocol ensure the effectiveness of the PPC therapy because the pacing periods may be interrupted for various reasons, and pacing pulses may not result in captured beats and hence may not contribute to the intended augmentation of myocardial mechanical stress. In one embodiment, protocol terminator 1558 also terminates the execution of the current pacing protocol in response to the termination command. This provides for safety control, for example, when the user decides that the execution of the current pacing protocol should be stopped for safety reasons.

Defibrillation output circuit 1578 deliver defibrillation pulses. Defibrillation control circuit 1577 controls delivery of the defibrillation pulses in response to a defibrillation command, which is another protocol execution command. This allows the user to apply a defibrillation therapy in response to an occurrence of tachyarrhythmia in the patient during the PPC therapy without the need for a separate defibrillator in addition to the external pacemaker.

User interface 1528 includes a command receiver 1565 that receives user commands, a parameter receiver 1564 that receives user parameters, and a presentation device 1566. In one embodiment, presentation device 1566 displays information allowing the user to monitor the execution of the current pacing protocol. Examples of such information include percentage of the current pacing protocol executed and selected pacing parameters used in the current pacing protocol. Sensing circuit 1560 senses one or more physiological signals, such as surface ECG signals sensed using surface electrodes or electrogram sensed using the electrodes in the PTVI devices. Physiological parameter detector 1561 detects the one or more physiological parameters using the sensed one or more physiological signals. Command/parameter producer 1562 produces the one or more protocol execution commands and the one or more protocol generation parameters using the user commands, the user parameters, and the detected one or more physiological parameters. In one embodiment, the patient's intrinsic heart rate is detected by physiological parameter detector 1561 using a signal sensed by sensing circuit 1560, and then used by protocol generator 1546 to set the pacing rate. In one embodiment, if a protocol generation parameter is a function of either a user parameter received by parameter receiver 1564 or a physiological parameter detected by physiological parameter detector 1561, its value is determined using the user parameter if available. In another words, a user parameter, if received, has priority over the corresponding detected physiological parameter. In one embodiment, command/parameter producer 1562 produces the protocol initiation command, the protocol termination command, and the defibrillation command using the user commands, as well as one or more sensed physiological parameters indicating occurrence and type of a tachyarrhythmia episode, for starting the PPC pacing sequence, stopping the PPC pacing sequence, and applying the defibrillation therapy.

In one embodiment, pacing system 1540 is constructed as part of external pacemaker 1222. Pacemaker chassis 1294 houses pacing output circuit 1424, pacing control circuit 1526, sensing circuit 1560, physiological parameter detector 1561, and command/parameter producer 1562. Protocol chassis 1295 houses pacing protocol module 1527. User interface 1528 is distributed in pacemaker user interface 1228 and protocol user interface 1274. In another embodiment, pacing system 1540 is constructed as part of external pacemaker 1322. Pacemaker chassis 1394 houses pacing output circuit 1424, pacing control circuit 1526, sensing circuit 1560, physiological parameter detector 1561, and command/parameter producer 1562. Protocol chassis 1395 houses pacing protocol module 1527. Pacemaker user interface 1328 includes user interface 1528.

Figure 16:
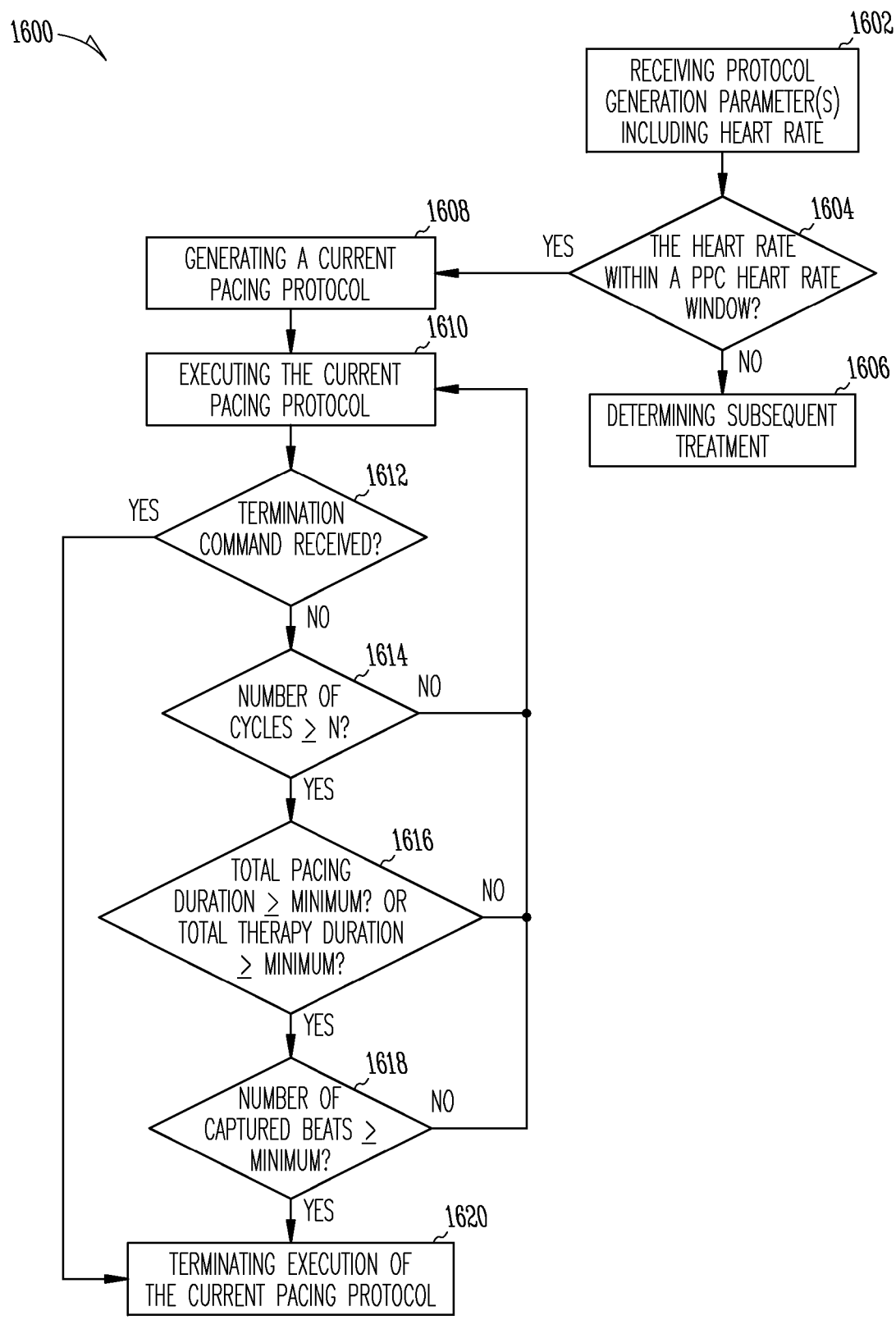
FIG. 16 is a flow chart illustrating an embodiment of a "smart PPC algorithm".

FIG. 16 is a flow chart illustrating an embodiment of a "smart PPC algorithm" 1600. Algorithm 1600 is to be applied to a post-MI patient, such as during a revascularization procedure. In one embodiment, a current pacing protocol executable by pacing control circuit 1426 or 1526 is generated according to algorithm 1600.

At 1602, one or more protocol generation parameters, including at least a heart rate, are received. In various embodiments, the one or more protocol generation parameters include one or more pacing parameters specified in the current pacing protocol and/or one or more physiological parameters used to calculate one or more pacing parameters specified in the current pacing protocol. In one embodiment, in addition to the heart rate, the one or more protocol generation parameters also include one or more parameters indicative of arrhythmia or other conditions affecting the PPC therapy.

At 1606, if the heart rate falls out of a PPC heart rate window specified by a minimum heart rate and a maximum heart rate at 1604, the current pacing protocol is not to be executed, and subsequent treatment for the patient is determined by the user. In one embodiment, the minimum heart rate is set between 40 and 70 beats per minute, with 50 beats per minute being a specific example, and the maximum heart rate is set between 120 and 160 beats per minute, with 140 beats per minute being a specific example. If the heart rate falls out of the PPC heart rate window, the user may determine, for example, that the PPC therapy is not indicated for the patient, that the PPC therapy should be delayed to wait for the heart rate to fall within the PPC heart rate window, or that a custom PPC protocol can be generated with pacing parameters appropriate for the measured heart rate.

At 1608, if the heart rate falls within the PPC heart rate window at 1604, the current pacing protocol is generated using one or more stored PPC protocols and the one or more protocol generation parameters. In one embodiment, a plurality of PPC protocols is stored. The current pacing protocol is generated by selecting a protocol from the plurality of PPC protocols based on the one and more protocol generation parameters. In another embodiment, the current pacing protocol is generated by receiving a stored PPC protocol and adjusting one or more pacing parameters specified in that stored PPC protocol based on the one or more protocol generation parameters. In one embodiment, generating the current pacing protocol includes setting a pacing rate (such as a lower rate limit) to a value exceeding the patient's heart rate by a specified margin, such as 10-20 beats per minute or a specified percentage of the patient's heart rate.

At 1610, the current pacing protocol is executed. The execution of the current pacing protocol is initiated in response to a protocol initiation command. In one embodiment, the protocol initiation command is entered by the user. In another embodiment, the protocol initiation command is automatically generated after the current pacing protocol is generated and the one or more physiological parameters indicate that the patient is ready to receive the PPC therapy. During the execution of the current pacing protocol, the pacing sequence including the alternating non-pacing and pacing periods is timed. This includes, for example, timing each of the non-pacing and pacing periods, timing a total pacing duration being the sum of the pacing periods, timing a total therapy duration being the sum of the pacing periods and non-pacing periods, and counting the number of cycles each including a non-pacing period followed by a pacing period. Whether the delivered pacing pulses each result in a captured beat (paced cardiac depolarization) is verified, and the number of the captured beats is counted upon the initiation of the execution of the current pacing protocol.

At 1620, the execution of the current pacing protocol is terminated if a termination command is received at 1612. The termination command is produced, for example, upon detection of an abnormal condition of the patient indicating a need to stop the PPC therapy for safety reasons.

If no termination command is received during the execution of the current pacing therapy, at 1620, the execution of the current pacing protocol is terminated if the number of cycles has reached a specified number (N) at 1614, the total pacing duration exceeds a specified minimum pacing time or the total therapy duration exceeds a specified minimum therapy time at 1616, and the number of the captured beats exceeds a specified minimum number at 1618. This completes the PPC therapy. If the number of cycles has not reached the specified number (N) at 1614, the total pacing duration does not exceed the specified minimum pacing time or the total therapy duration does not exceed the specified minimum therapy time at 1616, or the number of the captured beats does not exceed a specified minimum number at 1618, the current pacing protocol continues to be executed at 1610, by repeating the cycles of the alternating non-pacing and pacing periods.

Figure 17:
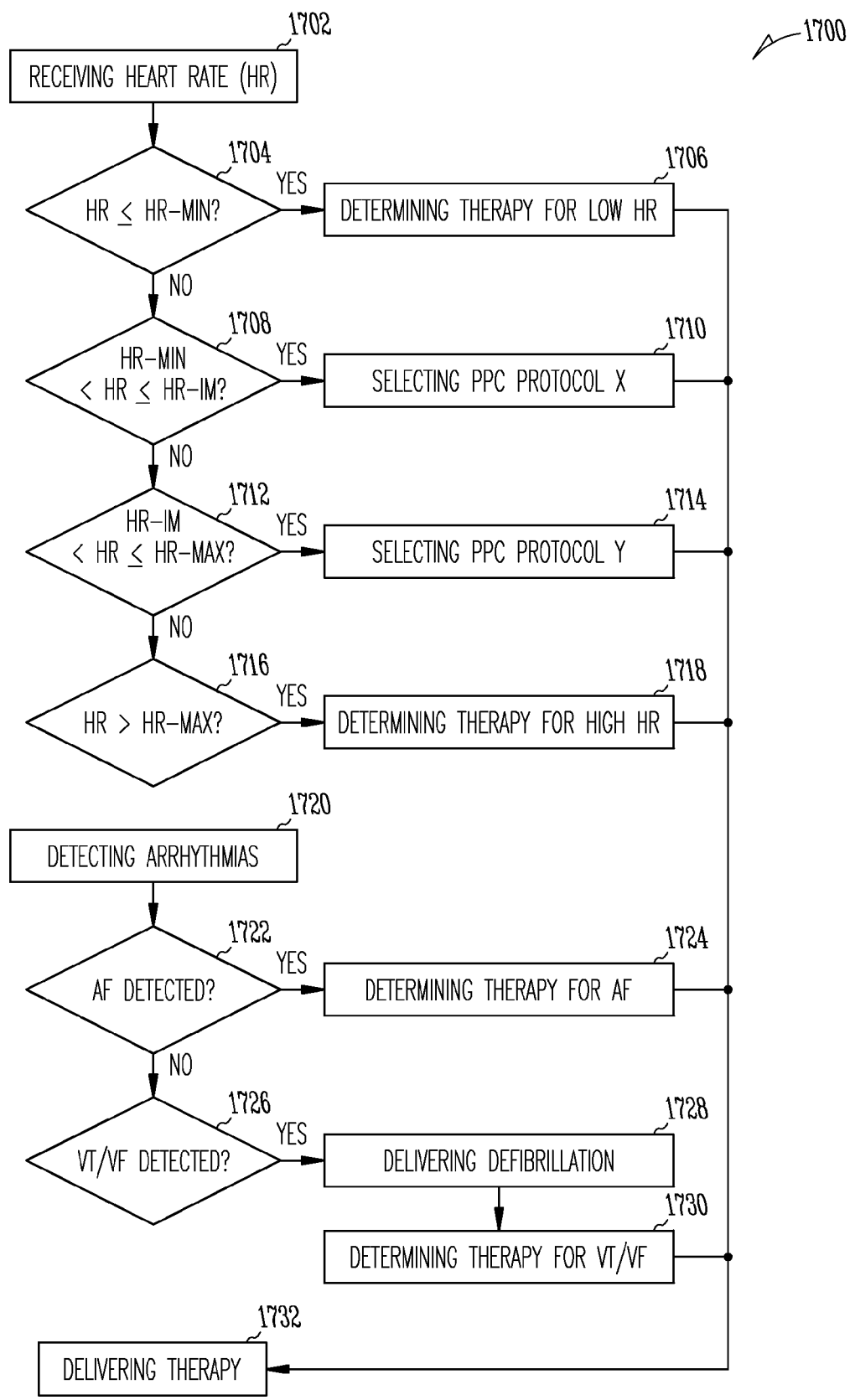
FIG. 17 is a flow chart illustrating an embodiment of a method for delivering a PPC therapy.

FIG. 17 is a flow chart illustrating an embodiment of a method 1700 for delivering a PPC therapy to a post-MI patient as an example of applying algorithm 1600. Specific quantities including specific parameter values and number of stored PPC protocols are presented by way of example, but not by way of limitation. In one embodiment, the PPC protocols are stored in storage device 1471 and executed by pacing control circuit 1426 or 1526 in a PPC therapy delivered using pacing system 1440 or 1540. Examples of the stored PPC protocols include PPC Protocols X and Y for different heart rate ranges, PPC protocols A and B for delivering PPC therapy while arrhythmia is detected, and custom PPC protocols.

PPC protocol X is for use when the patient heart rate falls within a low heart rate range (e.g., 50-100 beats per minute). PPC protocol X is for use when the patient heart rate falls within a high heart rate range (e.g., 100-150 beats per minute). If the number of pacing pulses delivered to augment mechanical stress on the myocardium depends on the intrinsic heart rate, such that when the pacing rate is programmed to exceed the intrinsic heart rate by a specified margin (e.g., 10-20 beats per minute), lower intrinsic heart rates mean fewer pacing pulses will be delivered. Thus, additional number of cycles and/or longer pacing periods may be required to ensure that the mechanical stress on the myocardium are augmented to a level sufficient to effect cardioprotection.

In one example, the non-pacing and pacing periods are each specified to be 30 seconds in both PPC protocols X and Y, while the number of cycles is specified to be 20 in PPC protocol X but 10 in PPC protocol Y. In another example, the number of cycles is specified to be 10 in both PPC protocols X and Y, while the non-pacing and pacing periods are each specified to be 60 seconds in PPC protocol X but 30 seconds in PPC protocol Y. In another example, the number of cycles is specified to be 10 in both PPC protocols X and Y, the non-pacing and pacing period is specified to be 30 seconds in both PPC protocols X and Y, and the non-pacing and pacing period is specified to be 60 seconds in PPC protocols X but 30 seconds in PPC protocol Y.

For illustrative purposes, Protocols X and Y are used for discussion as an example of PPC protocols for selection based on the patient's intrinsic heart rate. PPC protocols X and Y are provided for two ranges of the intrinsic heart rates. In various embodiments, two or more PPC protocols are provided each corresponding to a specified range of heart rates.

PPC protocols A and B are anti-arrhythmic PPC protocols for use when arrhythmic conditions are indicated for the patient receiving the PPC therapy. These anti-arrhythmic PPC protocols are used when the tachyarrhythmia such as atrial fibrillation, ventricular tachycardia, and ventricular fibrillation is detected in the patient before or during the PPC therapy. In one embodiment, anti-arrhythmic sub-threshold pacing is applied to stop the cycle of depolarization momentarily. In one embodiment, anti-arrhythmic PPC protocols A and B each specify a combination of parameters for anti-arrhythmic sub-threshold pacing. Examples of the parameters include pulse waveform (monophasic or biphasic), pulse amplitude (voltage), and pulse frequency. Protocol A is used first in response to the detection of a tachyarrhythmia episode. Protocol B is used if Protocol A fails to terminate the tachyarrhythmia episode.

For illustrative purposes, Protocols A and B are used for discussion as an example of anti-arrhythmic PPC protocols for selection based on effectiveness and/or parameters measured from the patient. PPC protocols A and B are provided for two combinations of anti-arrhythmic pacing parameters. In various embodiments, one or more anti-arrhythmic PPC protocols are provided each corresponding to one or more types of arrhythmias.

Custom PPC protocols are specifically tailored to an individual patient's specific conditions with which PPC protocols X, Y, A, and B are not suitable. In one embodiment, a custom PPC protocol is generated based on one or more template or default PPC protocols such as PPC protocols X, Y, A, and B, with one or more pacing parameters programmed by the user for the patient prior to the PPC therapy.

At 1702, the patient's heart rate (HR) is received. The heart rate is compared to a minimum heart rate (HR-MIN), a maximum heart rate (HR-MAX), and an intermediate heart rate (HR-IM) that is between the minimum and maximum heart rates. In one embodiment, the minimum heart rate is set between 40 and 70 beats per minute, with 50 beats per minute being a specific example, the maximum heart rate is set between 120 and 160 beats per minute, with 150 beats per minute being a specific example, and the intermediate heart rate is set between 71 and 119 beats per minute, with 100 beats per minute being a specific example. At 1706, a therapy for a patient with low heart rate is determined by the user if the heart rate is equal to or lower than the minimum heart rate at 1704. At 1710, PPC protocol X is selected if the heart rate is equal to or lower than the intermediate heart rate and higher than the minimum heart rate at 1708. At 1714, PPC protocol Y is selected if the heart rate is equal to or lower than the maximum heart rate and higher than the intermediate heart rate at 1712. At 1718, a therapy for a patient with high heart rate is determined by the user if the heart rate is higher than the maximum heart rate at 1716. The therapy for the patient with low heart rate and the therapy for the patient with high heart rate each include, for example, determining whether the patient's conditions are stable. If the conditions are not stable, the PPC therapy is not to be delivered to the patient, or modified to accommodate the patient's conditions. If the conditions are stable, the PPC therapy may proceed as determined by the user, using one of PPC protocol X, PPC protocol Y, and custom PPC protocols as selected by the user.

At 1720, arrhythmias are detected. In various embodiments, arrhythmias including atrial fibrillation (AF), ventricular tachycardia (VT) and ventricular fibrillation (VF) are detected before and during the delivery of the PPC therapy.

At 1724, a therapy for a patient with atrial fibrillation is determined by the user if atrial fibrillation is detected at 1722. At 1728, a defibrillation therapy is delivered when necessary as determined by the user if ventricular tachycardia or ventricular fibrillation is detected at 1726. At 1730, a therapy for a patient with ventricular tachycardia or ventricular fibrillation is determined by the user. The therapy for the patient with atrial fibrillation and the therapy for the patient with ventricular tachycardia or ventricular fibrillation each include determining stability of the patient's cardiac conditions. If the conditions are not stable, the PPC therapy is not to be delivered to the patient, or modified to accommodate the patient's conditions. If the conditions are stable, the PPC therapy may proceed as determined by the user, with one of PPC protocol A, PPC protocol B, and custom PPC protocols as selected by the user.

At 1732, the PPC therapy or other therapy as determined by the user is delivered to the patient. If the PPC therapy is delivered, a current pacing protocol is generated using the PPC protocol selected as discussed above. In one embodiment, if an arrhythmia is detected during the PPC therapy, the execution of the current pacing protocol is suspended or terminated, and the user determines how to proceed with the patient's conditions. If the user determines that the PPC therapy may continue, the execution of the current pacing protocol is resumed or restarted, with the current pacing protocol adjusted or regenerated if necessary.

It is to be understood that the above detailed description, including the various examples of cardioprotective pacing protocols and pacemakers, is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac pacing system, comprising:
   a pacing output circuit to deliver pacing pulses;
   a storage device;
   one or more pacing post-conditioning (PPC) protocols stored in the storage device, the one or more PPC protocols each specifying a pacing sequence including alternating non-pacing and pacing periods, the non-pacing periods each including a non-pacing duration during which no pacing pulse is timed to be delivered, the pacing periods each including a pacing duration during which a plurality of pacing pulses is timed to be delivered according to a stress augmentation pacing mode adapted to augment myocardial mechanical stress to a level effecting cardioprotection against myocardial injury;
   a pacing control circuit coupled to the pacing output circuit and the storage device, the pacing control circuit programmed to execute a current pacing protocol and including:
      a parameter input configured to receive one or more protocol generation parameters including at least one or more physiological parameters; and
      a protocol generator programmed to generate the current pacing protocol using the one or more PPC protocols and the one or more protocol generation parameters, the current pacing protocol specifying a plurality of pacing parameters, the one or more protocol generation parameters used to calculate one or more pacing parameters of the plurality of pacing parameters.

2. The system of claim 1, wherein the protocol generator is programmed to generate the current pacing protocol by selecting a protocol from the one or more PPC protocols using the one and more protocol generation parameters.

3. The system of claim 2, wherein the protocol generator is programmed to adjust one or more pacing parameters of the plurality of pacing parameters of the selected protocol using the one and more protocol generation parameters.

4. The system of claim 3, wherein the parameter input is configured to receive a heart rate, and the protocol generator is programmed to select the protocol from the one or more PPC protocols using the heart rate and adjust a pacing rate of the plurality of pacing parameters of the selected protocol using the heart rate.

5. The system of claim 2, further comprising a defibrillation output circuit to deliver defibrillation pulses, and wherein the parameter input is further configured to receive one or more parameters indicative of tachyarrhythmia, and the protocol generator is programmed to select the protocol from the one or more PPC protocols using the one or more parameters indicative of tachyarrhythmia.

6. The system of claim 1, wherein the pacing control circuit comprises:
   a protocol timer programmed to count a number of cycles each including a non-pacing period followed by a pacing period; and
   a protocol terminator programmed to terminate the execution of the current pacing protocol in response to the counted number of cycles reaching a specified number.

7. The system of claim 1, wherein the pacing control circuit comprises:
   a protocol timer programmed to time at least one of a total pacing duration and a total therapy duration, the total pacing duration being a sum of the pacing periods in the pacing sequence, the total therapy duration being a sum of the pacing periods and non-pacing periods in the pacing sequence; and a protocol terminator programmed to terminate the execution of the current pacing protocol in response to at least one of the total pacing duration exceeding a specified minimum pacing time and the total therapy duration exceeding a specified minimum therapy time.

8. The system of claim 1, wherein the pacing control circuit comprises:
a capture verifier programmed to verify whether each of the delivered pacing pulses results in a captured beat being a cardiac depolarization resulting from the each of the delivered pacing pulses;
a capture counter programmed to count a number of the captured beats; and
a protocol terminator programmed to terminate the execution of the current pacing protocol in response to the number of the captured beats detected during the pacing periods in the pacing sequence exceeding a specified minimum number of captured beats.

9. The system of claim 1, comprising
a pacemaker including:
a pacemaker chassis housing at least the pacing output circuit and the pacing control circuit; and
a pacing protocol interface coupled to the pacing control circuit; and
a pacing protocol module external to the pacemaker chassis and configured to be attached to the pacemaker and electrically connected to the pacing protocol interface, the pacing protocol module including the storage device.

10. The system of claim 9, wherein the pacemaker comprises:
a user interface incorporated onto the pacemaker chassis and including a command receiver configured to receive one or more user commands and a parameter receiver configured to receive one or more user parameters;
a sensing circuit to sense one or more physiological signals;
a physiological parameter detector to detect the one or more physiological parameters using the sensed one or more physiological signals; and
a command/parameter producer configured to produce one or more protocol execution commands and the one or more protocol generation parameters using the one or more user commands, the one or more user parameters, and the one or more physiological parameters,
and wherein the pacing control circuit is programmed to initiate and terminate the execution of the current pacing protocol in response to the one or more protocol execution commands.

11. A method for cardiac pacing, comprising:
receiving at least one pacing post-conditioning (PPC) protocol from a storage device storing one or more PPC protocols each specifying a pacing sequence, the pacing sequence including alternating non-pacing and pacing periods, the non-pacing periods each including a non-pacing duration during which no pacing pulse is timed to be delivered, the pacing periods each including a pacing duration during which a plurality of pacing pulses is timed to be delivered according to a stress augmentation pacing mode adapted to augment myocardial mechanical stress to a level effecting cardio protection against myocardial injury;
receiving one or more protocol generation parameters including at least one or more physiological parameters;
generating a current pacing protocol specifying a plurality of pacing parameters using the at least one PPC protocol and the one or more protocol generation parameters, including calculating one or more pacing parameters of the plurality of pacing parameters using the one or more protocol generation parameters;
controlling delivery of pacing pulses from a cardiac pacemaker by executing the current pacing protocol.

12. The method of claim 11, wherein receiving one or more protocol generation parameters comprises receiving a heart rate.

13. The method of claim 12, wherein the one or more PPC protocols comprises a plurality of PPC protocols, and generating the current pacing protocol comprises selecting a protocol from the plurality of PPC protocols using the heart rate.

14. The method of claim 13, wherein generating the current pacing protocol comprises setting a pacing rate of the plurality of pacing parameters to a value exceeding the heart rate by a specified margin.

15. The method of claim 11, wherein receiving one or more protocol generation parameters comprises receiving one or more parameters indicative of a type of arrhythmia, and generating the current pacing protocol comprises selecting a protocol from the plurality of PPC protocols based on the type of arrhythmia.

16. The method of claim 11, comprising
counting a number of cycles each including a non-pacing period followed by a pacing period; and
terminating the execution of the current pacing protocol in response to the counted number of cycles reaching a specified number.

17. The method of claim 11, comprising
timing at least one of a total pacing duration and a total therapy duration, the total pacing duration being a sum of the pacing periods in the pacing sequence, the total therapy duration being a sum of the pacing periods and non-pacing periods in the pacing sequence; and
terminating the execution of the current pacing protocol in response to at least one of the total pacing duration exceeding a specified minimum pacing time and the total therapy duration exceeding a specified minimum therapy time.

18. The method of claim 11, comprising:
verifying whether each of the delivered pacing pulses results in a captured beat being a cardiac depolarization resulting from the each of the delivered pacing pulses;
counting a number of the captured beats; and
terminating the execution of the current pacing protocol in response to the number of the captured beats detected during the pacing periods in the pacing sequence exceeding a specified minimum number of captured beats.

19. The method of claim 11, wherein receiving the at least one PPC protocol from the storage device comprises receiving the at least one PPC protocol from a pacing protocol module externally attached to the cardiac pacemaker, and comprising initiating the executing the current pacing protocol in response to an initiation command received by a user interface device incorporated onto a chassis of the cardiac pacemaker.

20. The method of claim 19, comprising terminating the executing the current pacing protocol in response to a termination command received by the user interface device.

* * * * *